(12) United States Patent
Zhang et al.

(10) Patent No.: US 8,093,566 B2
(45) Date of Patent: Jan. 10, 2012

(54) UPCONVERSION FLUORESCENT NANO-STRUCTURED MATERIAL AND USES THEREOF

(75) Inventors: Yong Zhang, Singapore (SG); Zhengguan Li, Singapore (SG)

(73) Assignee: National University of Singapore, Singapore (SG)

( * ) Notice: Subject to any disclaimer, the term of this patent is extended or adjusted under 35 U.S.C. 154(b) by 485 days.

(21) Appl. No.: 12/445,904

(22) PCT Filed: Oct. 17, 2007

(86) PCT No.: PCT/SG2007/000352
§ 371 (c)(1),
(2), (4) Date: Apr. 16, 2009

(87) PCT Pub. No.: WO2008/048190
PCT Pub. Date: Apr. 24, 2008

(65) Prior Publication Data
US 2011/0127445 A1    Jun. 2, 2011

(51) Int. Cl.
*G01J 1/58* (2006.01)
(52) U.S. Cl. ................................ 250/459.1
(58) Field of Classification Search .......... 250/458.1, 250/459.1; 252/301.35, 582; 359/326; 424/9.6, 424/78.18; 428/407; 435/180
See application file for complete search history.

(56) References Cited

U.S. PATENT DOCUMENTS

| | | | |
|---|---|---|---|
| 2003/0030067 A1* | 2/2003 | Chen | 257/102 |
| 2007/0037215 A1* | 2/2007 | Patton | 435/7.1 |
| 2007/0087195 A1* | 4/2007 | Meyer et al. | 428/403 |
| 2009/0081461 A1* | 3/2009 | Yi et al. | 428/407 |

FOREIGN PATENT DOCUMENTS

| | | |
|---|---|---|
| GB | 2 413 334 A | 10/2005 |
| WO | WO 2005/015213 A1 | 2/2005 |
| WO | WO 2006/131226 A1 | 12/2006 |
| WO | WO 2007/078262 A1 | 7/2007 |

OTHER PUBLICATIONS

D. Chatterjee et al., "Novel Nanodevice for Cancer Immunotherapy" Fourth International Nanomedicine and Drug Delivery Symposium, p. 84, Oct. 8, 2006.

Q. Li et al., "Luminescence of Europium(III) and Terbium(III) Complexes Incorporated in Poly(Vinyl Pyrrolidone) Matrix" Journal if Physical Chemistry B, vol. 105, pp. 12293-12296, Nov. 16, 2001.

(Continued)

*Primary Examiner* — David Porta
*Assistant Examiner* — Marcus Taningco
(74) *Attorney, Agent, or Firm* — Dickstein Shapiro LLP

(57) ABSTRACT

Upconversion fluorescent nano-structured material(s) comprising at least one compound of formula $(M_1)_j(M_2)_kX_n$:$(M_3)_q$ and at least one polymer, wherein: each X is the same or different and is selected from the group consisting of: halogen, O, S, Se, Te, N, P and As; each $M_1$, if present, is the same or different and is selected from the group consisting of: Li, Na, K, Rb, Cs, Fr, Be, Mg, Ca, Sr, Ba, Ra, O and $NH_4$; each $M_2$ is the same or different and is a metal ion; each $M_3$, independently, is the same or different and is selected from the group consisting of Sc, Y, La, Ce, Pr, Nd, Pm, Sm, Eu, Gd, Tb, Dy, Ho, Er, Tm, Yb and Lu; j is $0 \leq j \leq 10$; k is $1 \leq k \leq 10$; n is $1 \leq n \leq 10$; and q is $1 \leq q \leq 10$. In particular, the polymer is wherein the polymer soluble in polar solvents.

26 Claims, 15 Drawing Sheets

OTHER PUBLICATIONS

H. Mai et al., "High-Quality Sodium Rare-Earth Fluoride Nanocrystals: Controlled Synthesis and Optical Properties" Journal of the American Chemical Society, vol. 128, pp. 6426-6436, Apr. 20, 2006.

E. Ricci-Júnior et al., "Zinc(II) Phthalocyanine Loaded PLGA Nanoparticles for Photodynamic Therapy Use" International Journal of Pharmaceutics, vol. 310, No. 1-2, pp. 187-195, Mar. 9, 2006.

F. Wang et al., "Luminescent Nanomaterials for Biological Labelling," Nanotechnology, vol. 17, pp. R1-R3, 2006.

E. Beaurepaire, et al., "Functionalized Fluorescent Oxide Nanoparticles: Artificial Toxins for Sodium Channel Targeting and Imaging at the Single-Molecule Level," Nano Letters, vol. 4, No. 11, pp. 2079-2083, 2004.

H. Sertchook et al., "Submicron Silica/Polystyrene Composite Particles Prepared by a One-Step Sol-Gel Process," Chemistry of Materials, vol. 15, No. 8, pp. 1690-1694, 2003.

F. van de Rijke, et al., "Up-Converting Phosphor Reporters for Nucleic Acid Microarrays," Nature Biotechnology, vol. 19, pp. 273-276, Mar. 2001.

G. Yi, et al., "Synthesis, Characterization, and Biological Application of Size-Controlled Nanocrystalline $NaYF_4$:Yb,Er Infrared-to-Visible Up-Conversion Phosphors," Nano Letters, vol. 4, No. 11, pp. 2191-2196, 2004.

J.F. Suyver et al., "Novel Materials Doped with Trivalent Lanthanides and Transition Metal Ions Showing Near-Infrared to Visible Photon Upconversion," Optical Materials, vol. 27, pp. 1111-1130, 2005.

K.W. Kramer, et al., "Hexagonal Sodium Yttrium Fluoride Based Green and Bllue Emitting Upconversion Phosphors," Chemistry of Materials, vol. 16, No. 7, pp. 1244-1251, 2004.

S. Heer, et al., "Highly Efficient Multicolour Upconversion Emission in Transparent Colloids of Lanthanide-Doped $NaYF_4$ Nanocrystals," Advanced Materials, vol. 16, No. 23-24, pp. 2102-2105, Dec. 2004.

D.R. Larson, et al., "Water-Soluble Quantum Dots for Multiphoton Fluorescence Imaging in Vivo," Science, vol. 300, No. 5624, pp. 1434-1436, 2003.

J-H Zeng, et al., "Synthesis and Upconversion Luminescence of Hexagonal-Phase $NaYF_4$:Yb, $Er^{3+}$Phosphors of Controlled Size and Morphology," Advanced Materials, vol. 17, pp. 2119-2123, 2005.

J-C Boyer, et al., "Synthesis of Colloidal Upconverting $NaYF_4$ Nanocrystals Doped with $Er^{3+}Yb^{3+}$and $Tm^{3+}$, $Yb^{3+}$via Thermal Decomposition of Lanthanide Trifluoroacetate Precursors," Journal of the American Chemical Society, vol. 128, pp. 7444-7445, 2006.

Y. Yang, et al., "A Gold Nanocomposite Made Soluble in Both Water and Oil by the Addition of a Second Adsorption Layer of Poly-N-Vinyl-2-Pyrrolidone on Gold Nanoparticles that have been Made Hydrophobic," Nanotechnology, vol. 17, pp. 461-465, 2006.

D.M.L. Goodgame, et al., "A Macrobicyclic Bimetallic Chain Polymer Incorporating Deprotonated 2-Pyrrolidone Bridges," Angewandte Chemie-International Edition in English, vol. 27, No. 2, pp. 261-262, 1988.

Y. Gao, et al., "Silver Nanowires with Five-Fold Symmetric Cross Section," Journal of Crystal Growth, vol. 276, pp. 606-612, 2005.

M. Liu, et al., "An Investigation of the Interaction Between Polyvinylpyrrolidone and Metal Cations," vol. 44, pp. 55-64, 2000.

R. Si, et al., "Self-Organized Monolayer of Nanosized Ceria Colloids Stabilized by Poly(vinylpyrrolidone)," Journal of Physical Chemistry B, vol. 110, pp. 5994-6000, 2006.

C. Graf, et al., "A General Method for the Controlled Embedding of Nanoparticles in Silica Colloids," Langmuir, vol. 22, No. 13, pp. 5604-5610, 2006.

C. Graf, et al., "A General Method to Coat Colloidal Particles with Silica," Langmuir, vol. 19, No. 17, pp. 6693-6700, 2003.

T. Nann, et al., "Single Quantum Dots in Spherical Silica Particles," Angewandte Chemie International Edition, vol. 43, No. 40, pp. 5393-5396, 2004.

D.K. Yi, et al., "Silica-Coated Nanocomposites of Magnetic Nanoparticles and Quantum Dots," Journal of the American Chemical Society, vol. 127, No. 14, pp. 4990-4991, 2005.

T-J. Yoon, et al., "Specific Targeting, Cell Sorting and Bioimaging with Smart Magnetic Silica Core-Shell Nanomaterials," Small, vol. 2, No. 2, pp. 209-215, 2006.

* cited by examiner

UPCONVERSION FLUORESCENT NANO-STRUCTURED MATERIAL AND USES THEREOF

FIELD OF THE INVENTION

The present invention relates to upconversion fluorescent nano-structured material(s) and methods for their preparation and used thereof. In particular, the invention related to upconversion fluorescent nanoparticles, methods for their preparation and uses thereof.

BACKGROUND OF THE ART

Nano-sized fluorescent labeling materials have been widely used for biological studies and clinical applications. Conventional down-conversion fluorescent labels require ultraviolet or blue excitation wavelength (Beaurepaire et al. 2004; Wang et al. 2006). These single-photon fluorescent labels emit one lower energy photon after absorbing higher energy UV or visible photon. Their disadvantages include low light penetration depth and possible severe photo-damage to living organisms. Furthermore, many biological samples show auto fluorescence under short wavelength UV radiation, which decreases the sensitivity of detection. The use of fluorescent labels that can be excited in the near infrared (NIR) region was suggested (Sertchook and Avnir 2003). Yi et al. 2004 and van de Rijke et al. 2001, suggested the infrared-to-visible up-conversion nanocrystal. These nanocrystals emit one higher energy photon after absorbing two or more lower-energy photons. Different colors of visible light can be obtained from different up-conversion phosphors when excited by the same IR laser (van de Rijke et al. 2001). In comparison with down-conversion fluorescent materials, up-conversion nanocrystals show very low background light due to their unique fluorescent properties. In addition, photodamage to biological tissues is minimal because these tissues are usually transparent to NIR light (Suyver et al. 2005). Among the most commonly used up-conversion nanocrystals, Yb/Er or Yb/Tm co-doped $NaYF_4$ nanocrystals have been reported as efficient infrared-to-visible up-conversion material (Kramer et al. 2004). Colloidal Yb/Er and Yb/Tm co-doped $NaYF_4$ nanocrystals have been prepared with strong up-conversion fluorescence seven orders of magnitude higher than that of CdSe—ZnS quantum dots (Heer et al. 2004; Larson et al. 2003).

Some efforts have been made to produce up-conversion $NaYF_4$ nanocrystals with controlled size and shape (Heer et al. 2004; Yi et al. 2004; Zeng et al. 2005). Ethylenediamine tetraacetic acid (EDTA) was used as a chelating agent to control the growth of $NaYF_4$ nanocrystals, but the nanocrystals as prepared tended to precipitate in solution (Yi et al. 2004; Zeng et al. 2005). Colloidal solutions of $NaYF_4$ nanocrystals were prepared. However, these nanocrystals were hydrophobic and could only be dispersed in certain organic solvents such as hexane and dimethyl sulfoxide (DMSO) under ultrasound sonication (Boyer et al. 2006; Heer et al. 2004; Mai et al. 2006). Use of these nanocrystals directly for bio-applications is very limited due to their very small solubility in water and unsuitable surface property.

Accordingly, there is still a need in this field of technology of improved upconversion nanoparticles. In fact, the synthesis of monodisperse and water soluble fluoride nanocrystals with upconversion fluorescence is still very challenging. In particular, there is a need in developing suitable methods for synthesizing up-conversion $NaYF_4$ nanocrystals which are dispersible in water and organic solvents and have some functional chemical groups on their surfaces for conjugation of biomolecules (Larson et al. 2003).

SUMMARY OF THE INVENTION

The present invention addresses the problems above, and in particular to provide new and improved upconversion fluorescent nano-structured material(s). In particular, there are provided new and improved nano-sized phosphors with upconversion (UC) fluorescence which have great potential for use in biological studies and clinical applications, as labeling materials, imaging probes, and the like.

According to a first aspect, the present invention provides at least one upconversion fluorescent nano-structured material comprising at least one compound of formula $(M_1)_j(M_2)_k X_n:(M_3)_q$ and at least one polymer, wherein each X is the same or different and is selected from the group consisting of: halogen, O, S, Se, Te, N, P and As;

each $M_1$, if present, is the same or different and is selected from the group consisting of: Li, Na, K, Rb, Cs, Fr, Be, Mg, Ca, Sr, Ba, Ra, O and $NH_4$;

each $M_2$ is the same or different and is a metal ion;

each $M_3$, independently, is the same or different and is selected from the group consisting of Sc, Y, La, Ce, Pr, Nd, Pm, Sm, Eu, Gd, Tb, Dy, Ho, Er, Tm, Yb and Lu;

j is $0 \leq j \leq 10$; k is $1 \leq k \leq 10$; n is $1 \leq n \leq 10$; and q is $1 \leq q \leq 10$.

In particular, $M_2$ may be selected from the group consisting of: transition metal ions, inner transition metal ions, and Group I to Group VI metal ions. In particular, $M_2$ may be selected from the group consisting of: Sc, Y, La, Ce, Pr, Nd, Pm, Sm, Eu, Gd, Tb, Dy, Ho, Er, Tm, Yb and Lu. Each $M_3$, independently, is the same or different and may be selected from the group consisting of: Yb, Er, Tm and Ho.

Accordingly to a particular embodiment (when j is zero), $M_1$ is not present and the compound of the invention has formula $(M_2)_k X_n:(M_3)_q$.

In the upconversion fluorescent nano-structured material according to the invention wherein the compound has formula $(M_2)_k X_n:(M_3)_q$ or $(M_1)_j(M_2)_k X_n:(M_3)_q$, when q is 1, only $M_3$ element is doped in the nano-structured material. A particular non-limiting example for this embodiment is $NaYF4:Yb$. When q is 2 (or a higher value), two (or more) preferably different $M_3$ elements are co-doped into the nano-structured material. A particular non-limiting example for this embodiment (when q is 2) is $NaYF4:Yb,Er$ With reference to the polymer, it may be a linear polymer or a branched polymer. It may be amphiphilic or hydrophilic. In particular, the polymer is a polymer soluble and/or dispersible in polar solvents, for example in water. The polymer may be a polymer having an amino group. The polymer may have an average molecular weight of about 5-50 kDa, for example, about 10-40 kDa, about 15-25 kDa. In particular, the polymer has an average molecular weight of about 25 kDa. The polymer may be selected from the group consisting of: polyethylenimine (PEI), poly-l-lysine (PLL), polyvinylpyrrolidone (PVP), polyvinyl alcohol (PVA), poly(ethylene glycol) (PEG), poly(4 vinylpyridine) (P4VP), oleic acid, stearic acid, chitosan and mixtures thereof. In particular, the polymer is PEI, PVP or a mixture thereof. More in particular, the polymer is PEI. The nano-structured material according to the invention may comprise the polymer at a concentration of about 5-50 weight %, in particular, of about 10-25 weight %.

According to particular examples, the compound of formula $(M_1)_j(M_2)_k X_n:(M_3)_q$ may be selected from the group consisting of: $NaM_2F_4:(M_3)_q$, $LiM_2F_4:(M_3)_q$, $KM_2F_4:(M_3)_q$, $RbM_2F_4:(M_3)_q$, $CsM_2F_4:(M_3)_q$, $BeM_2F_5:(M_3)_q$, $Be(M_2)_2F_8$:

$(M_3)_q$, $MgM_2F_5:(M_3)_q$, $Mg(M_2)_2F_8:(M_3)_q$, $CaM_2F_5:(M_3)_q$, $Ca(M_2)_2F_8:(M_3)_q$, $SrM_2F_5:(M_3)_q$, $Sr(M_2)_2F_8:(M_3)_q$, $BaM_2F_5:(M_3)_q$, $Ba(M_2)_2F_8:(M_3)_q$, $M_2F_3:(M_3)_q$, $(M_2)_2O_2S:(M_3)_q$, $(M_2)_2O_3S:(M_3)_q$, $(M_2)_2O_3:(M_3)_q$ and a combination thereof, wherein $M_2$ and $M_3$ are as defined through the whole content of the present application. More in particular, when q is 2, the nano-structured material according to the invention may be selected from the group consisting of: $PEI/NaYF_4$; $PEI/NaYF_4:Yb,Er$; $PEI/NaYF_4:Yb,Tm$; $PEI/NaYF_4:Yb,Ho$; $PVP/NaYF_4$; $PVP/NaYF_4:Yb,Er$; $PVP/NaYF_4:Yb,Tm$; $PVP/NaYF_4:Yb,Ho$ and a combination thereof.

The upconversion fluorescent nano-structured material according to the invention may have a structure selected from the group consisting of: spherical, hexagonal, cubic, tetragonal, rhombohedral, orthorhombic, monoclinic, triclinic and a combination thereof. For example, the nano-structured material has a hexagonal structure. According to particular examples, the nano-structured material may be hexagonal phase $NaYF_4$, hexagonal phase $NaYF_4:Yb,Er$, hexagonal phase $NaYF_4:Yb,Tm$ or hexagonal phase $NaYF_4:Yb,Ho$.

The upconversion fluorescent nano-structured material according to the invention may have at least one dimension of sizes $\leq 100$ nm. For example, $\leq 50$ nm, $\leq 20$ nm or $\leq 10$ nm.

The upconversion fluorescent nano-structured material according to any preceding claim, wherein the nano-structured material is at least one nanoparticle and the average diameter of the nanoparticle(s) is $\leq 100$ nm. The nano-structured material according to the invention may be at least one nanoparticle and the average diameter of the nanoparticle(s) is $\leq 50$ nm.

The upconversion fluorescent nano-structured material according to the invention may be in the form of: nanoparticle(s), nanofilm or monolith. In particular, the nano-structured material according to the invention may be a NIR-to-visible upconversion fluorescent nanoparticle.

The upconversion fluorescent nano-structured material according to the invention may further comprise at least one surfactant, lipid, polymer, inorganic material, or a mixture thereof which is disposed about the nano-structured material and modifies the surface of the nano-structured material.

The upconversion fluorescent nano-structured material according to the invention may further comprise at least one layer of silica which is disposed about the nano-structured material and which modifies the surface of the nano-structured material. According to this embodiment the layer of silica is applied on the nano-structured material to form a core-shell structure.

The upconversion fluorescent nano-structured material according to the invention may further comprise at least one photosensitizer which is disposed about the nano-structured material and modifies the surface of the nano-structured material. The photosensitizer may be any suitable photosensitizer suitable for the purpose of the invention. In particular, the photosensitizer may be Zinc phthalocyanine (ZnPC), aminolevulinic acid (ALA), methyl aminolevulinate, temoporfin, phtalocyanine, and the like. Any other photosensitizer available in the art and suitable for the purpose of the present invention may also be used.

The upconversion fluorescent nano-structured material according to the invention may further comprise at least one biomolecule. The biomolecule may be attached to the nano-structured material. The biomolecule may be selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

There is also provided at least one article of manufacture comprising the upconversion fluorescent nano-structured material according to any aspect of the invention. The article of manufacture may be at least one of the following: a display device, a solar cell, an optical data storage, a bio-probe, a carrier for drug delivery, a lamp, a LED, a LCD, a wear resistance, a laser, optical amplifier, and/or a device for bio-imaging. However, further article of manufacture know or obvious to a skilled person are also encompassed by the scope of the present invention.

There is also provided a kit comprising at least one nano-structured material or an article of manufacture according to any one aspect of the invention. The kit may, optionally, comprise at least one biomolecule.

There is also provided at least one bio-imaging and/or bio-detection apparatus comprising: at least one upconversion fluorescent nano-structured material according to any aspect of the invention; at least one biomolecule; at least one source of excitation; and at least one means for delivery of the source of excitation to the system. The source of excitation may be NIR. In particular, the NIR is at 980 nm. The means for delivery of the source of excitation to the apparatus may be selected from the group consisting of: optical fibres, endoscopes, external light and external laser.

There is also provided a upconversion fluorescent nano-structured material according to the invention for use in medicine. In particular, there is provided a upconversion fluorescent nano-structured material according to the invention for use in photodynamic therapy or for use in non-invasive imaging. In particular, the photodynamic therapy is in cancer cells. There is also provided the use of at least one upconversion fluorescent nano-structured material according to any aspect of the invention in the preparation of a medicament for photodynamic therapy.

There is also provided a method for photodynamic therapy, the method comprising the step of administering to a subject the upconversion fluorescent nano-structured material according to any aspect of the invention.

There is also provided a method of preparing at least one upconversion fluorescent nano-structured material according to any aspect of the invention, comprising: mixing ions of at least one $M_3$ and at least one $M_2$ to obtain a mixture; adding at least one polymer to the mixture; and adding ions of at least one X. The method may further comprise adding the polymer in the presence of ions of at least one M1.

There is also provided a method of controlling the size and/or shape of the upconversion fluorescent nano-structured material(s) comprising varying the amount of polymer in the upconversion fluorescent nano-structured material.

NaYF$_4$:Yb,Er (C, total fluorescence; D, E, fluorescence passing through filters for red and green light respectively) and PVP/NaYF$_4$:Yb,Tm.

Figure 5:
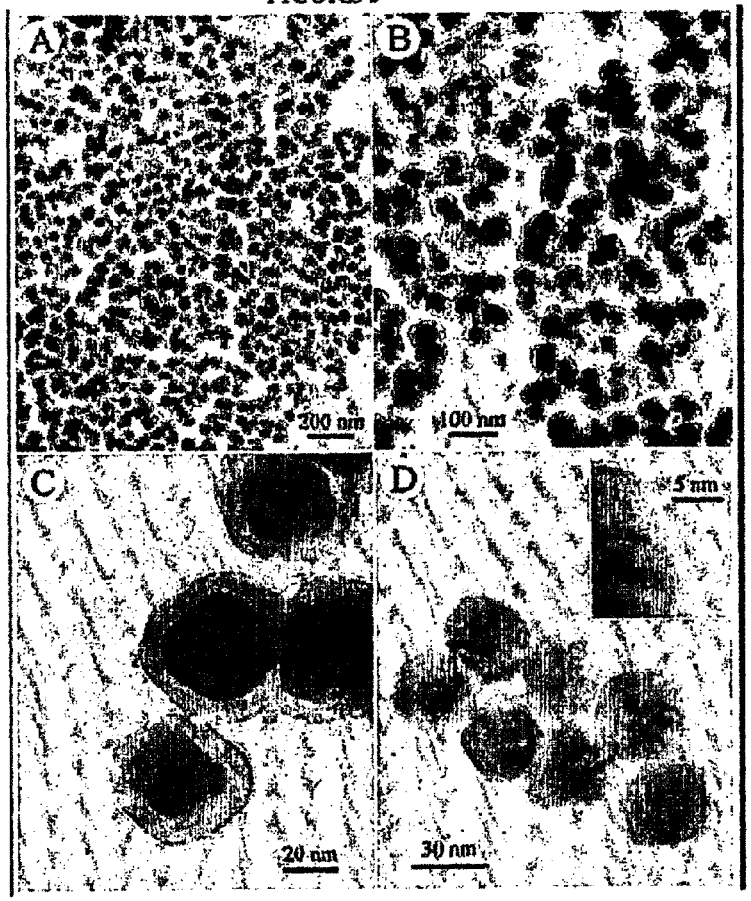

FIG. 5. TEM images of silica coated PVP/NaYF$_4$:Yb,Er nanocrystals (A, B, C). TEM image of PVP/NaYF$_4$:Yb,Er nanocrystals coated with a very thin silica layer is also given (D).

Figure 6:
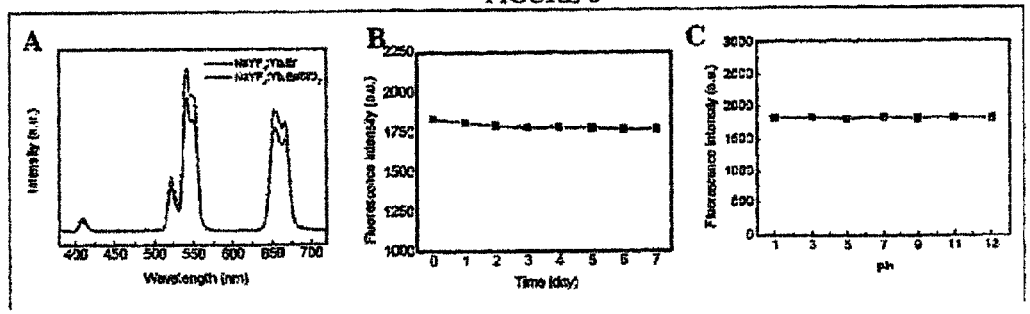

FIG. 6. Fluorescence spectra of NaYF$_4$:Yb,Er nanocrystals before (dot line) and after (solid line) silica coating (A) and fluorescence intensity of the silica coated nanocrystals in water as a function of time (B) and pH (C).

Figure 7:
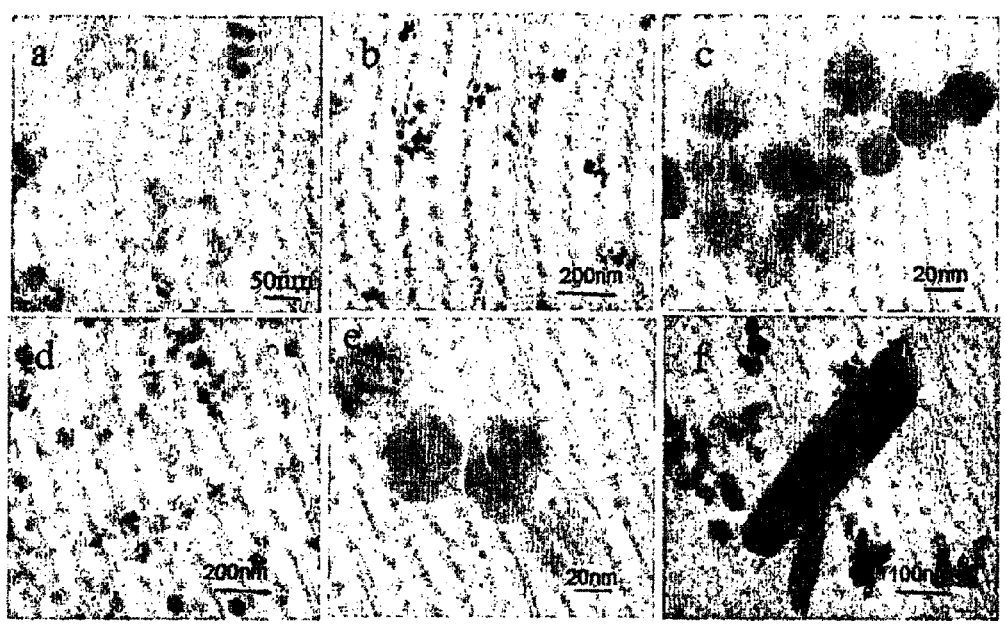

FIG. 7. TEM images of PEI/NaYF$_4$:Yb$^{3+}$,Er$^{3+}$ nanocrystals with (a) 5 wt %, (b,c) 10 wt %, (d,e) 25 wt %, (f) 50 wt % PEI concentration.

Figure 8:
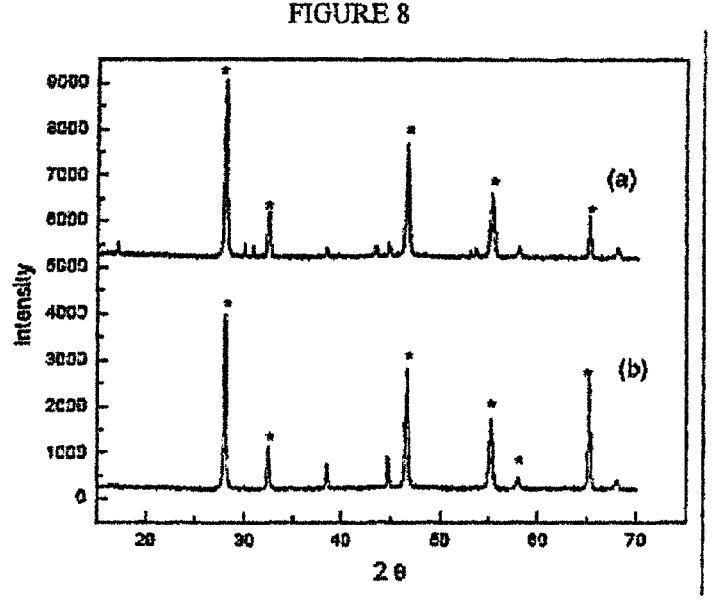

FIG. 8: XRD data of sample (a) with 10 wt % (b) with 25 wt % PEI concentration.

Figure 9:
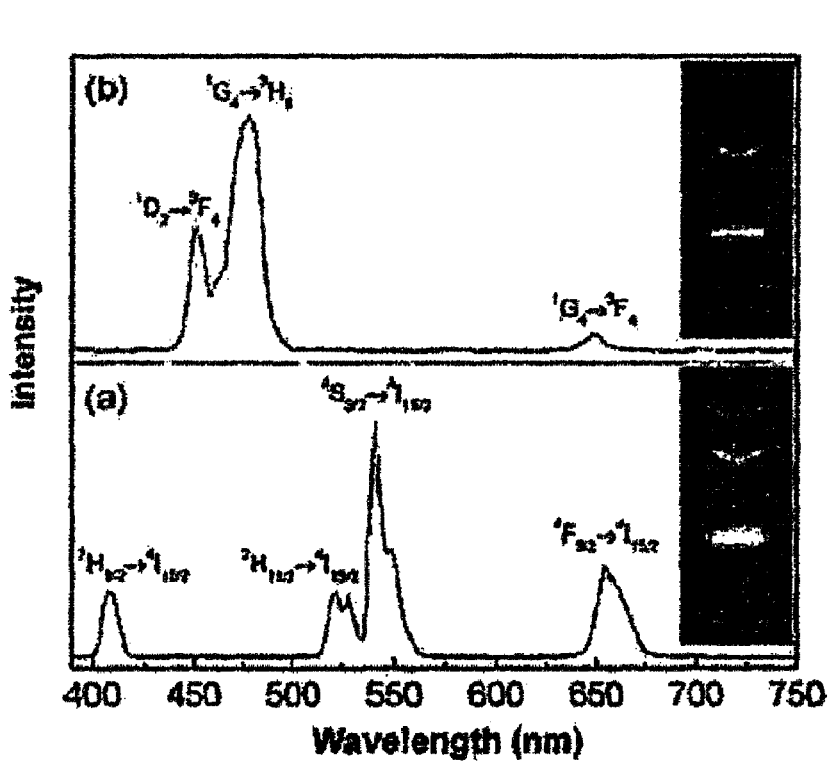

FIG. 9. NIR-to-visible upconversion fluorescence spectra and photographs of the PEI/NaYF$_4$:Yb$^{3+}$,Er$^{3+}$ (a) and PEI/NaYF4:Yb$^{3+}$,Tm$^{3+}$ (b) nanoparticles in aqueous solutions, excited using a NIR laser.

Figure 10:
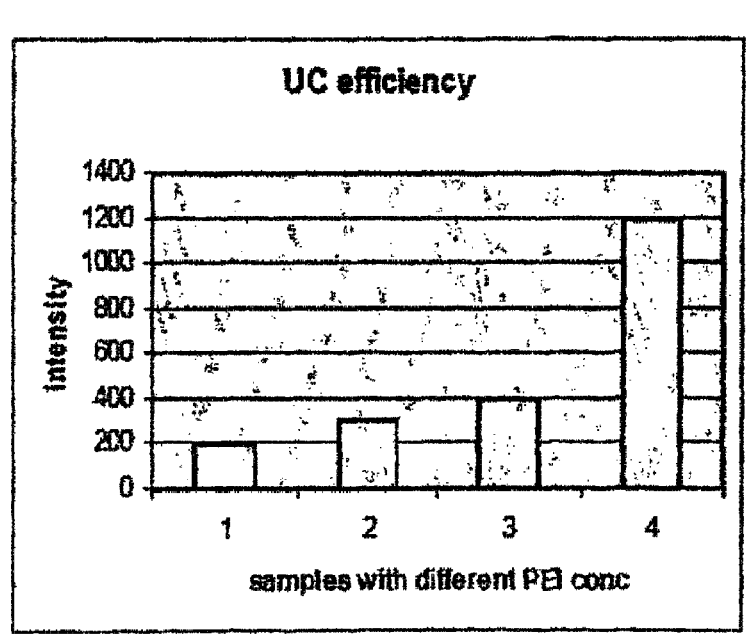
Figure 11:
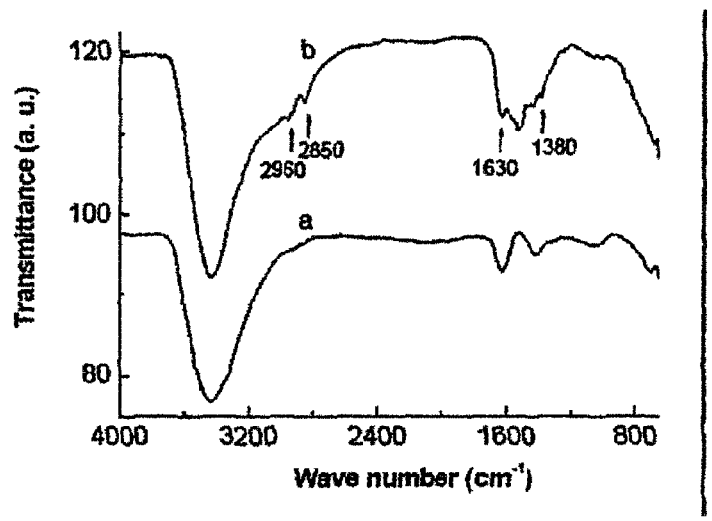

FIG. 10: The up conversion fluorescence spectra samples with: 1) pure NaYF$_4$:Yb$^{3+}$, Er$^{3+}$; 2) 5 wt %; 3) 10 wt %; 4) 25 wt % PEI/NaYF$_4$:Yb$^{3+}$, Er$^{3+}$ FIG. 11. FT-IR spectra of pure NaYF$_4$:Yb,Er (a) and PEI/NaYF$_4$:Yb,Er (b) nanocrystals.

Figure 12:
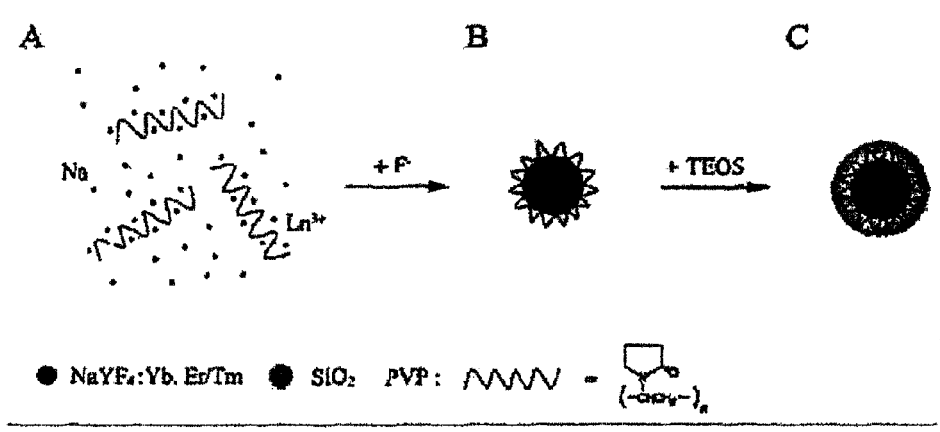

FIG. 12. Scheme of synthesis of silica coated PVP/NaYF$_4$ nanocrystals doped with lanthanide ions.

Figure 13:
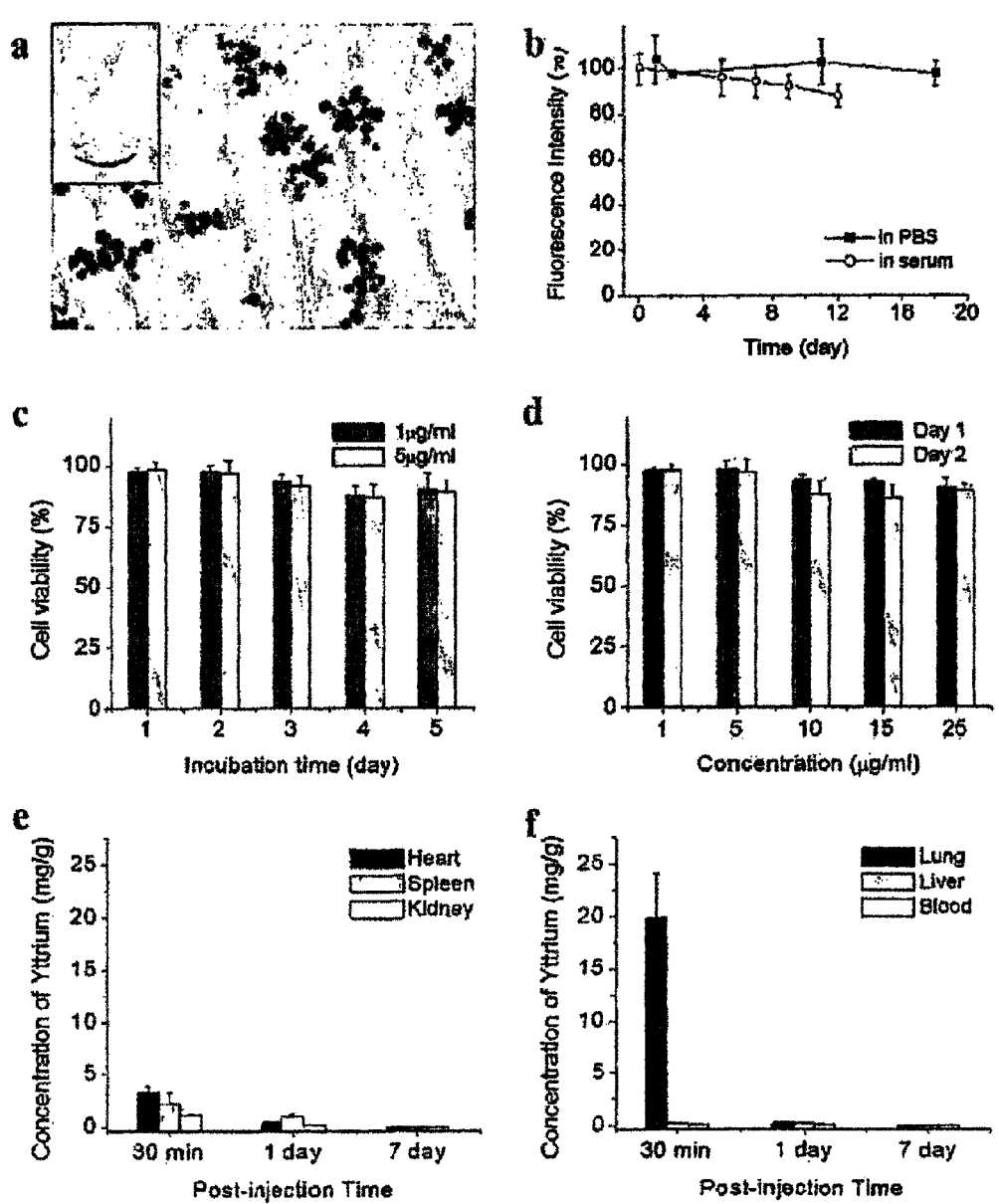

FIG. 13. PEI/NaYF4 upconversion nanoparticles. (a) TEM image of PEI/NaYF4 nanoparticles showing monodisperse nanoparticles with approximately 50 nm in size. Insert, Photograph of the nanoparticles in PBS demonstrating the monodispersity by the clear solution of the nanoparticles. (b) Fluorescence intensity of PEI/NaYF4:Yb,Er nanoparticles in PBS and serum as a function of incubation time. Viability of bone marrow derived stem cells after incubated with the nanoparticles for different time periods (c) and the nanoparticles with different concentrations (d). (e,f) Biodistribution of the nanoparticles in organs of rat harvested at different time after tail-vein injection of the nanoparticles. (All bars denote standard error, n=4).

Figure 14:
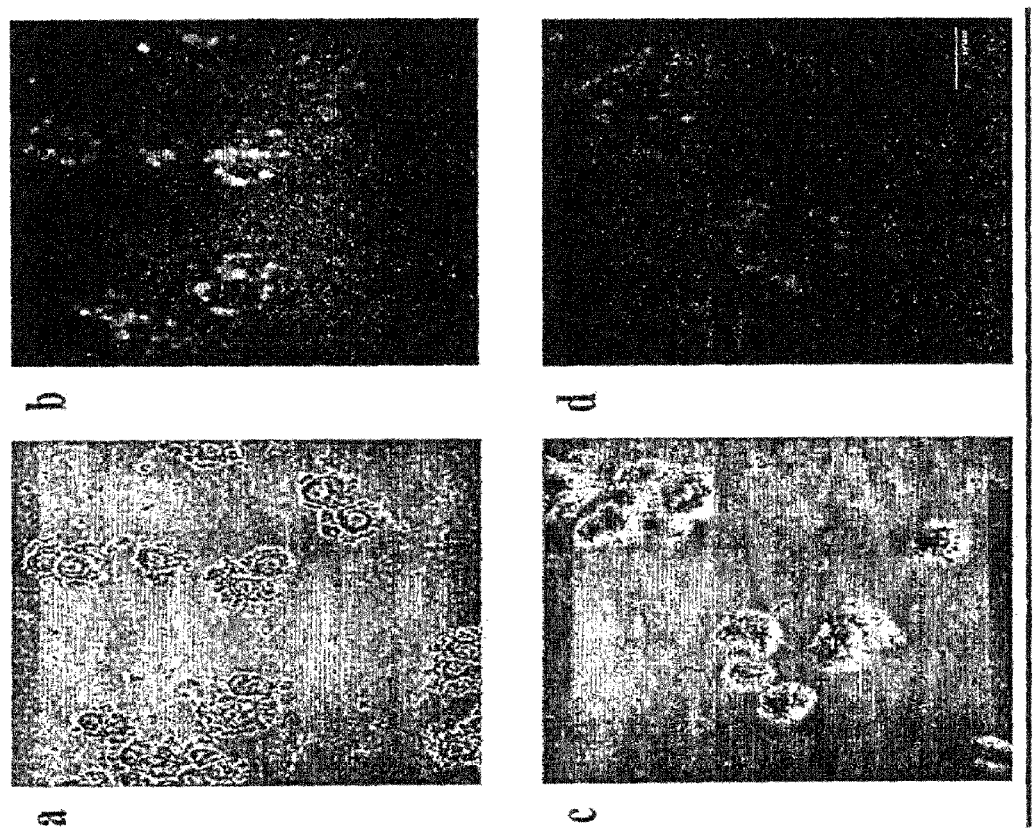

FIG. 14. Imaging of cells incubated with PEI/NaYF4:Yb,Er nanoparticles. Bright field (a,c) and confocal fluorescence (b,d) images of human colonic adenocarcinoma cells (HT29, a,b) and human breast cancer cells (SKBR3, c,d) incubated with folic acid functionalized PEI/NaYF4 nanoparticles for 1 hour.

Figure 15:
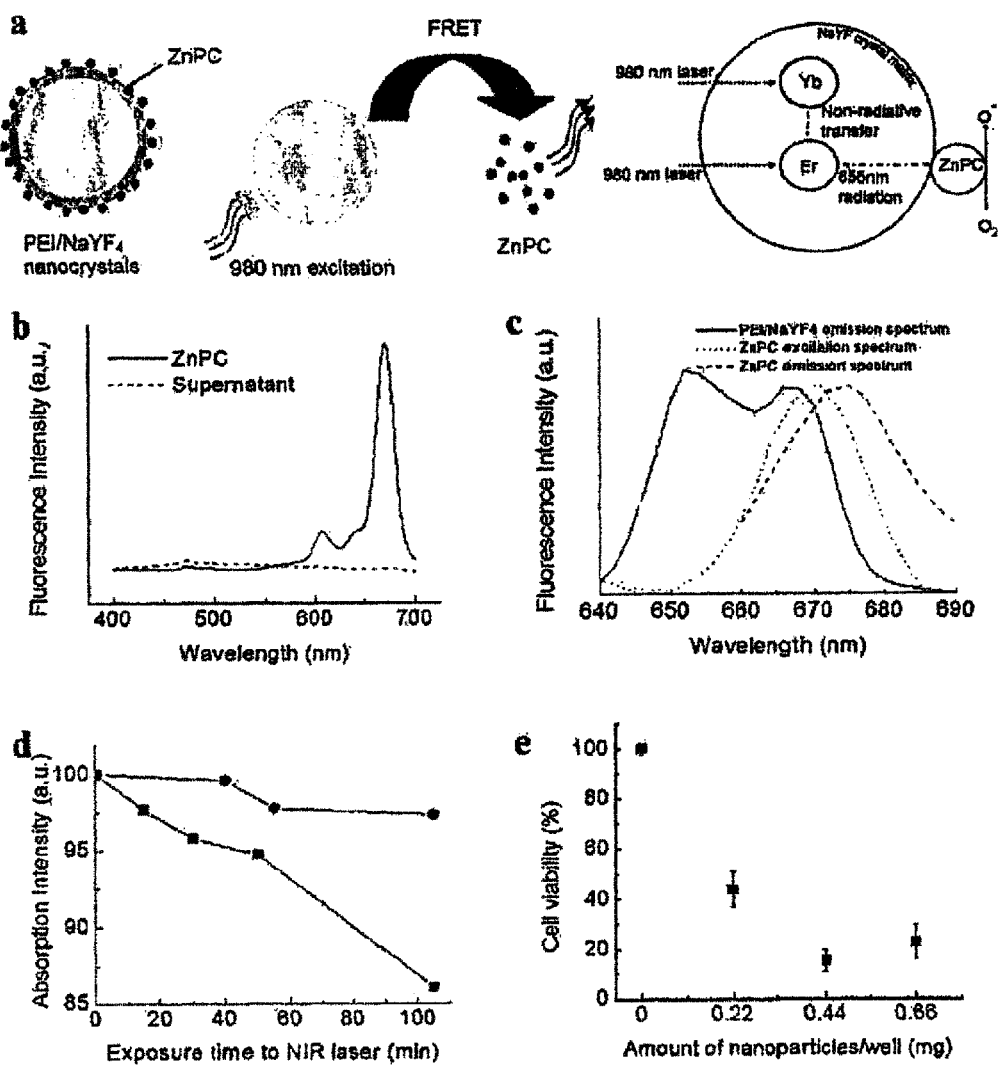

FIG. 15. Photodynamic therapy using PEI/NaYF4:Yb,Er nanoparticles attached with ZnPC. (a) Schematic drawing showing how photodynamic therapy works using upconversion nanoparticles. Upon exposure to NIR light, the nanoparticles convert NIR light to visible light which will activate the photosensitizer ZnPC to produce reactive oxygen species to kill cancer cells. (b) Fluorescence spectra of ZnPC attached to the nanoparticles and that in the supernatant, after ZnPC was mixed with the nanoparticles and then the nanoparticles were centrifuged. Encapsulation efficiency calculated from the standard curve of fluorescence emission spectra of ZnPC before and after attachment to the nanoparticles is determined to be approximately 97%. (c) Fluorescence emission spectra of PEI/NaYF4:Yb,Er nanoparticles when excited with 980 nm NIR laser (solid line) overlaps considerably with excitation spectra of ZnPC (dashed line) (d). ADPA destruction representing singlet oxygen production (measured by absorption intensity at 400 nm) as a function of exposure time to NIR laser shows steady fall from original (100%) for the ZnPC-PEI/NaYF4:Yb,Er nanoparticles (squares) while pure ADPA control undergoes slight bleaching on continuous exposure to laser (circles) (e). MTT assay to demonstrate the effectiveness of the nanoparticles for photodynamic therapy, by measuring the viability of HT29 cells after exposed to 980 nm laser for 5 minutes, after incubation with different amount of ZnPC-PEI/NaYF4:Yb,Er nanoparticles for 24 hours (Bars show standard error, n=4).

Figure 16:
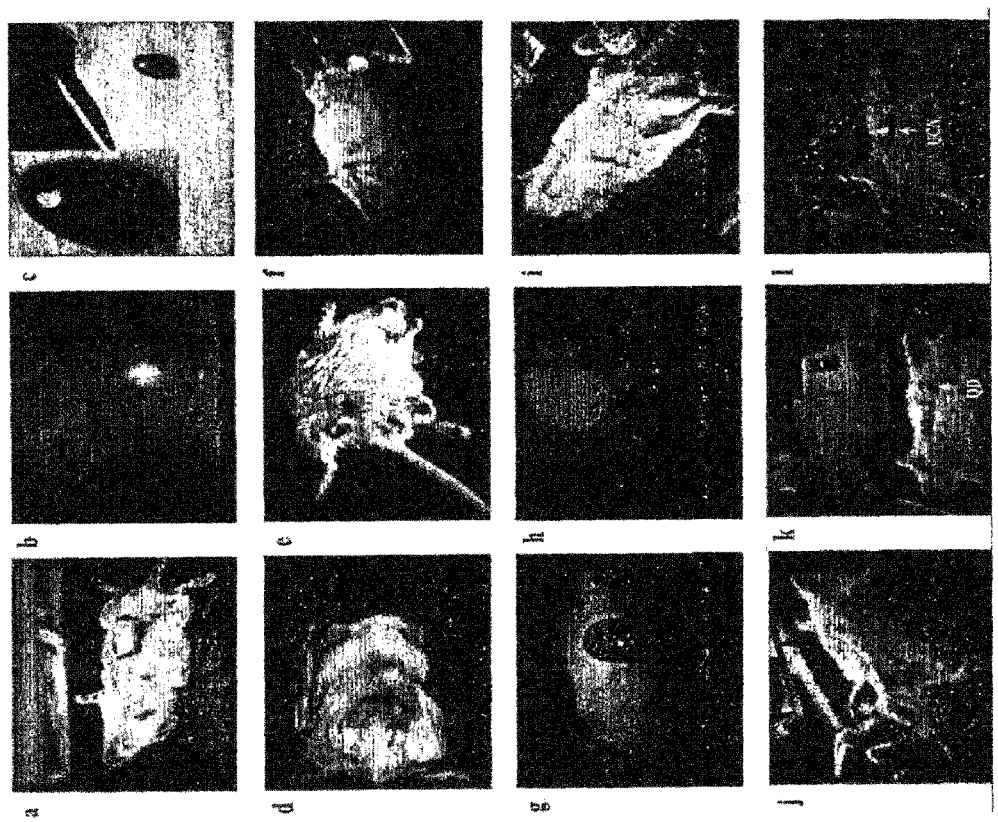

FIG. 16. imaging of mice and rats injected with quantum dots and PEI/NaYF4:Yb,Er upconversion nanoparticles. Intradermal injection of quantum dots (a) and PEI/NaYF4:Yb,Er nanoparticles (b) into mice both demonstrated visible fluorescence. However, only the latter showed luminescence when injected into deeper tissues such as heart (c), back muscles (d), groin muscles (e) and thigh muscles (f). Intradermal injection of quantum dots into dorsal skin of rats showed no fluorescence (g, back skin as compared to quantum dot sample placed on dish) but some fluorescence was seen from thinner foot skin (h). In contrast, fluorescence from upconversion nanoparticles injected into muscles of the groin was seen through intact skin (i) or when exposed (j). Intradermal injection of quantum dots (to an approximate depth of 10 mm) on shaved rat abdominal skin did not show fluorescence upon excitation with a UV lamp (k). Similar injection of upconversion nanoparticles showed fluorescence upon excitation with a NIR laser (l). The middle square was injected with PBS as control. These demonstrated the superior luminescence depth of upconversion nanoparticles and the ability to image deeper tissues and/or to use photodynamic therapy at these depths.

Figure 17:
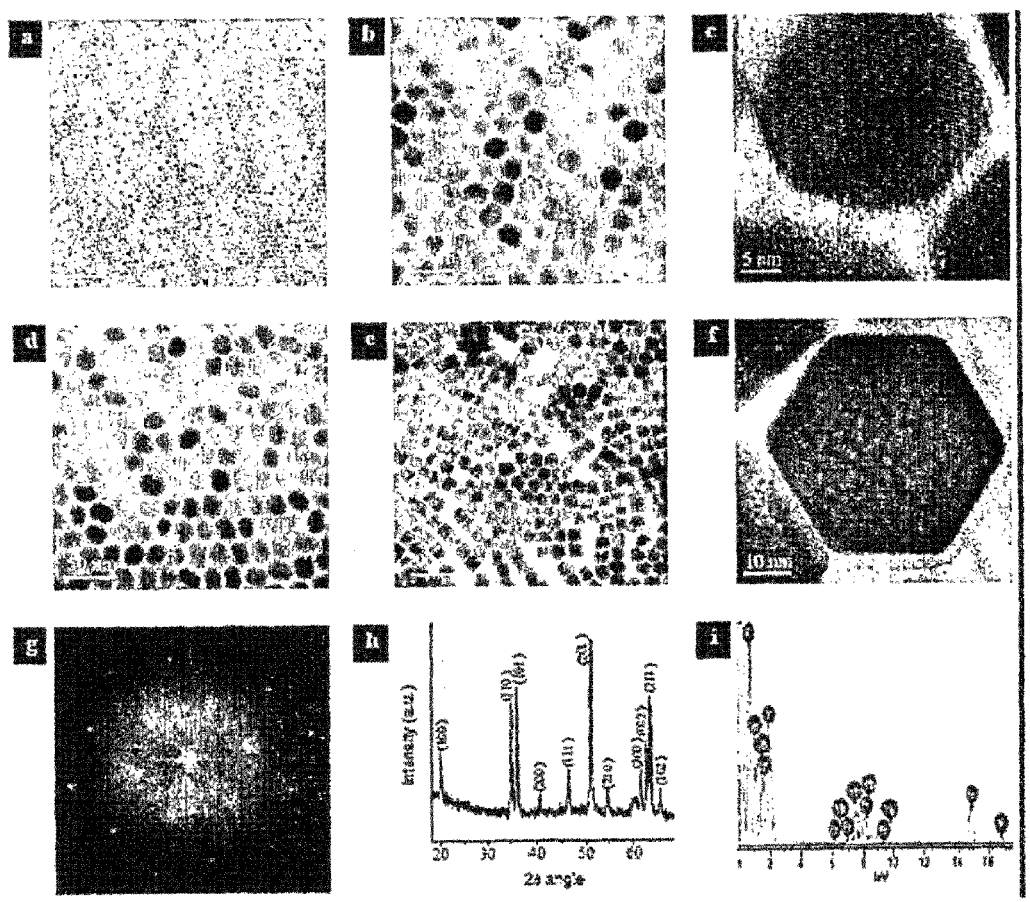

FIG. 17. Control of nanocrystal shape. a-c. TEM images of NaYF4:Yb,Er nanospheres at different magnifications. d, TEM images of NaYF4:Yb,Er nanoellipses. e,f, TEM images of NaYF4:Yb,Er nanoplates at different magnifications. g, Fourier Transform of TEM image in f. XRD pattern (h) and EDAX analysis (i) of NaYF4:Yb,Er nanospheres.

Figure 18:
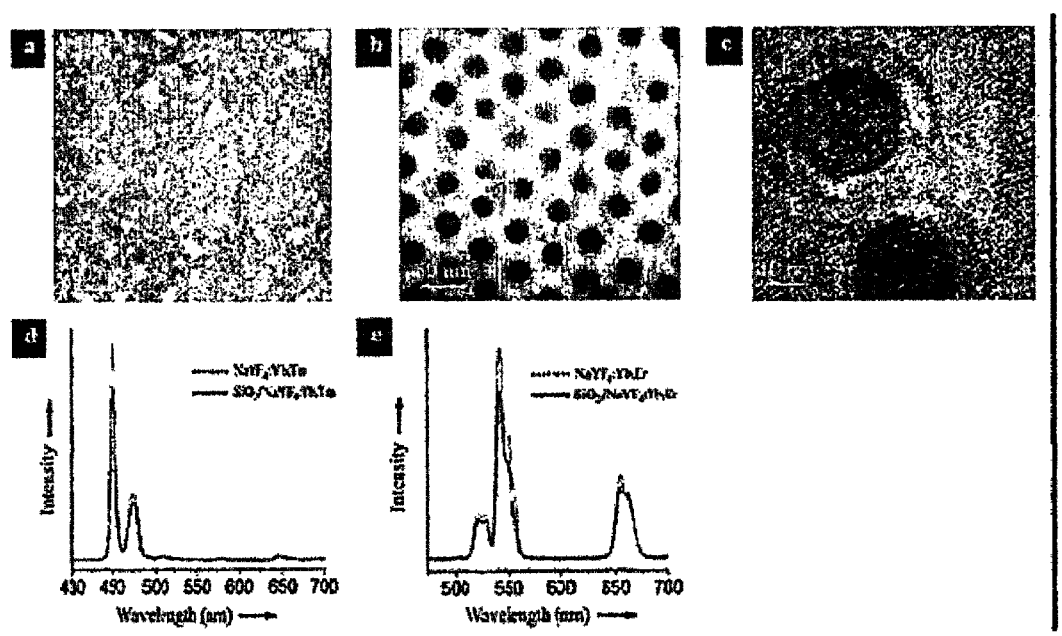

FIG. 18. Coating of silica on nanocrystals. TEM images of silica coated NaYF4:Yb,Er nanospheres at different magnifications (a-c) and fluorescence spectra of NaYF4:Yb,Tm (d) and NaYF4:Yb,Er (e) nanospheres with and without silica coating.

Figure 19:
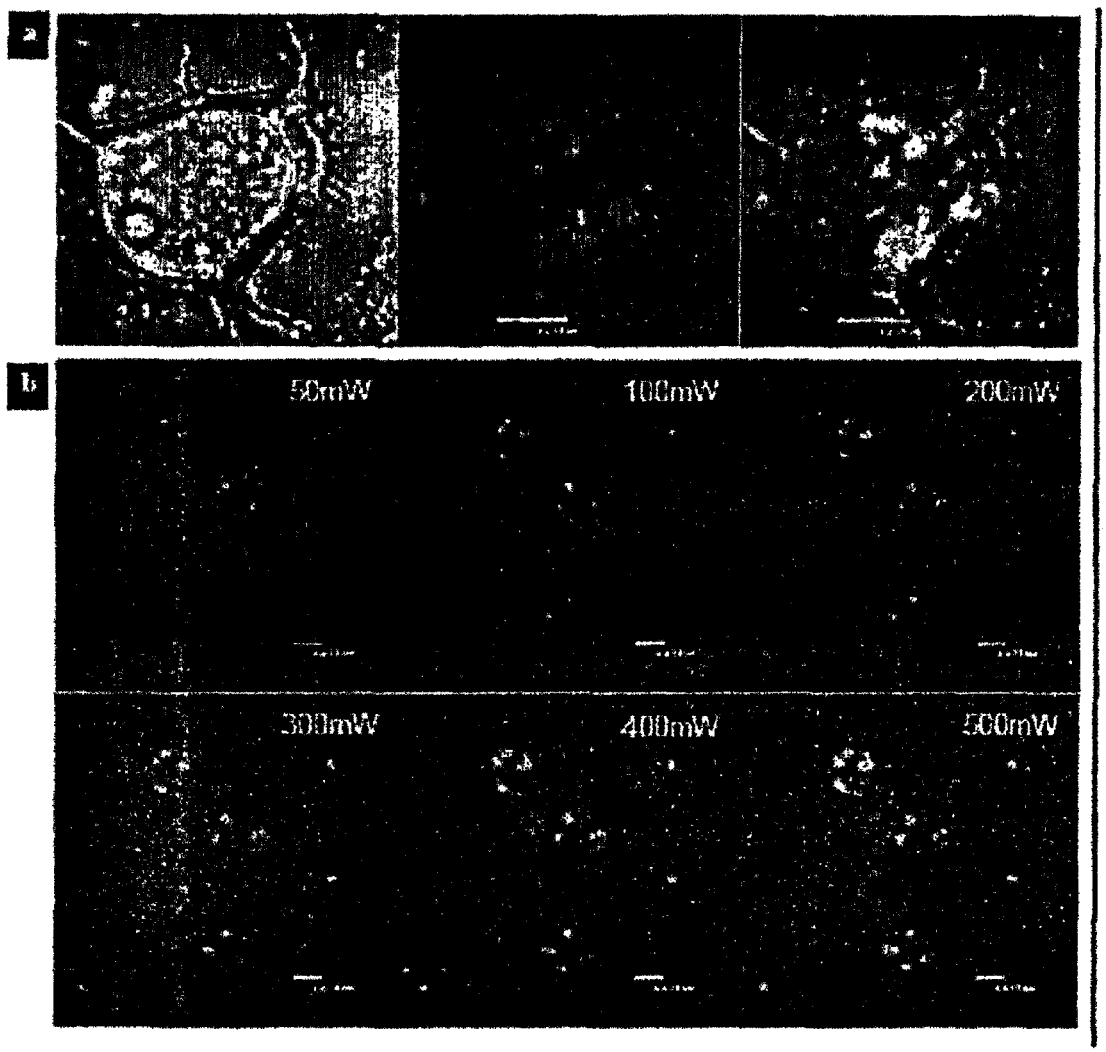

FIG. 19. Confocal fluorescence imaging of MCF-7 cells using silica/NaYF4:Yb,Er nanospheres. a, Bright-field (left), confocal fluorescence (middle) and superimposed (right) images of MCF-7 cells incubated with the nanospheres for 24 hours. b, Confocal fluorescence images of MCF-7 cells with the nanospheres excited by 980 nm laser at different power intensities.

Figure 20:
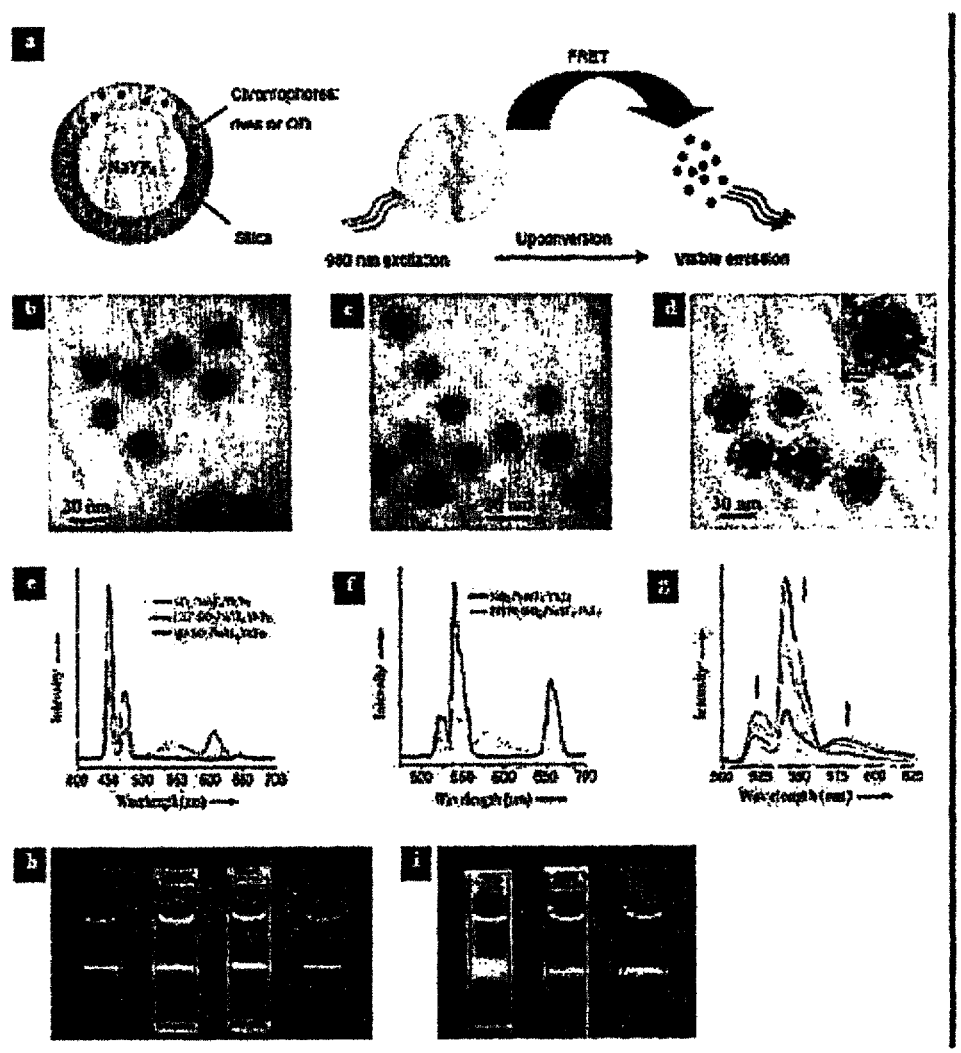

FIG. 20. Multi-color NIR-to-visible upconversion nanospheres. a, Schematic drawing of FRET based multi-color silica/NaYF4 NIR-to-visible upconversion nanospheres. TEM images of FITC doped silica/NaYF4:Yb,Tm nanospheres (b), TRITC doped silica/NaYF4:Yb,Er nanospheres (c), and QD605 doped silica/NaYF4:Yb,Tm nanospheres (d). e, fluorescence spectra of pure silica/NaYF4:Yb,Tm nanospheres (black line) and the nanospheres doped with FITC (green line) and QD605 (red line). f, fluorescence spectra of pure silica/NaYF4:Yb,Er nanospheres (black line) and the nanospheres doped with TRITC (red line). g, fluorescence spectra of silica/NaYF4:Yb,Er nanospheres (0.01 mmol) doped with different amount of TRITC (10, 20, 30, 40 nmol). h, photographs of silica/NaYF4 nanospheres in hexane (1 wt %) under excitation of NIR laser (980 nm, power density=50 Wcm-2): total upconversion fluorescence of NaYF4:Yb,Tm nanospheres (blue), total upconversion fluorescence of NaYF4:Yb,Er nanospheres (yellow green) and fluorescence passing through red (green) or green (red) filters. i, photographs showing total fluorescence of FITC doped silica/NaYF4:Yb,Tm nanospheres (left), TRITC doped silica/

NaYF4:Yb,Er nanospheres (middle) and QD605 doped silica/NaYF4:Yb,Tm nanospheres (right).

DETAILED DESCRIPTION OF THE INVENTION

Bibliographic references mentioned in the present specification are for convenience listed in the form of a list of references and added at the end of the examples. The whole content of such bibliographic references is herein incorporated by reference.

During the past decade, the preparation of up-conversion phosphors with small grain size began to receive growing attraction because they are considered to meet a wide variety of other applications, such as volumetric display and lamps. Use of upconversion phosphors as biological labels has attracted even more interest. However, nanometer-sized phosphors with mono-dispersed size distribution and highluminescent efficiency is required as a labeling material for biomolecules, especially for sensitive determination of molecules such as DNA, RNA or proteins. Although a lot of literatures dealing with lanthanide doped down-conversion luminescent nanoparticles have been reported, lanthanide doped up-conversion nanoparticles have received little attention. As the phenomenon of up-conversion is an important process for the generation of visible light from near-infrared radiation, a rare-earth or transition-metal ion doped material should produce a population in an excited state whose energy exceeds the pump photon. Rare-earth ions such as Pr3+, Nd3+, Sm3+, Dy3+, Ho3+, Er3+ and Tm3+ have all demonstrated up-conversion and particularly suited to undergo this process as they possess several excited states with long lifetimes that are well matched to the emission wavelengths of several efficient pump laser sources. The lanthanide-doped nanoparticles are usually made in high-temperature or bombardment experiments. Only a small number of lanthanide-doped nanoparticles that are synthesized at low temperature have been reported previously.

The present invention provides new upconversion fluorescent nano-structured material(s) comprising at least one polymer and method(s) for its preparation. In particular, the upconversion fluorescent nano-structured material according to the invention are useful in applications such as bio-imaging, photodynamic therapy, bio-detection, and the like. However, its application may not be limited to this list.

In particular, the present invention relates to fluoride nanocrystals with strong upconversion fluorescence emission, which are well dispersed in water and most commonly used organic solvents to form colloidal solutions.

For the purpose of the present invention the term "nanoparticle" and "nanocrystal" may be used interchangeably.

In this invention, ultrafine pure phase fluoride nanocrystals doped with lanthanide ions, such as Er or Tm, are synthesized using at least one polymer, for example PVP or PEI, as a chelating agent and/or stabilizer. The nanocrystals are very uniform in size and the size is tunable by changing the experimental conditions. Furthermore, the nanocrystals are monodisperse in water and some most commonly used organic solvents, and strong multi-color up-conversion fluorescence can be observed from the clear colloidal solution of the nanocrystals under excitation of NIR laser. Moreover, a uniform layer of silica may be coated onto the nanocrystals to form a core-shell structure with the thickness adjustable, which provides a suitable surface for conjugation of biomolecules. Furthermore, PEI may also be used as a surfactant to control the growth of the nanocrystals and functionalize their surfaces. The amino groups of PEI existing on the nanocrystals may be used directly for attachment of biomolecules.

These nano-sized phosphors with upconversion fluorescence have great potential for use in biological studies and clinical applications, as labeling materials, imaging probes, and the like.

According to one aspect, the present invention provides at least one nano-structured material comprising at least one compound of formula $(M_1)_j(M_2)_kX_n:(M_3)_q$ and at least one polymer, wherein each X, independently, is the same or different and is selected from the group consisting of: halogen, O, S, Se, Te, N, P and As;

each $M_1$, if present, is the same or different and is selected from the group consisting of: Li, Na, K, Rb, Cs, Fr, Be, Mg, Ca, Sr, Ba, Ra, O and $NH_4$;

each $M_2$, independently, is the same or different and is a metal ion;

each $M_3$, independently, is the same or different and is selected from the group consisting of Sc, Y, La, Ce, Pr, Nd, Pm, Sm, Eu, Gd, Tb, Dy, Ho, Er, Tm, Yb and Lu;

j is $0 \leq j \leq 10$; k is $1 \leq k \leq 10$; n is $1 \leq n \leq 10$; and q is $1 \leq q \leq 10$.

In particular, $M_2$ may be selected from the group consisting of: transition metal ions, inner transition metal ions, and Group I to Group VI metal ions. In particular, $M_2$ may be selected from the group consisting of: Sc, Y, La, Ce, Pr, Nd, Pm, Sm, Eu, Gd, Tb, Dy, Ho, Er, Tm, Yb and Lu. Each $M_3$, independently, is the same or different (preferably different) and may be selected from the group consisting of: Yb, Er, Tm and Ho, or a combination thereof, such as Yb—Er, Yb—Ho, or Yb—Tm.

One or more $M_3$ according to any aspect of the present invention may be used to act as the dopant. A dopant may be an impurity which is added to a compound in low concentrations to alter some properties of the compound. For example, a dopant may be added in a concentration ranging from one part in a thousand to one part in ten million. It would be understood that a dopant does not alter the crystal structure of the compound it is added to. For example, a dopant may be added to a nano-structured material prepared according to the method of any aspect of the present invention so that the nano-structured material can have additional or enhanced properties. The properties include, but are not limited to, optical properties, magnetic properties, electrical properties and fluorescence.

Accordingly to a particular embodiment (Wherein j is zero), $M_1$ is not present and the compound of the invention has formula $(M_2)_kX_n:(M_3)_q$.

In the upconversion fluorescent nano-structured material according to the invention wherein the compound has formula $(M_2)_kX_n:(M_3)_q$ or $(M_1)_j(M_2)_kX_n:(M_3)_q$, when q is 1, only $M_3$ element is doped in the nano-structured material. A particular non-limiting example for this embodiment is NaYF4:Yb. When q is 2 (or a higher value), two (or more) preferably different $M_3$ elements are co-doped into the nano-structured material. A particular non-limiting example for this embodiment is NaYF4:Yb,Er.

In particular, j is $1 \leq j \leq 10$, for example 1, 2, 3, 4 or 5, more in particular j is 1. k is $1 \leq k \leq 10$, for example 1, 2, 3, 4, or 5, more in particular k is 1. n is $1 \leq n \leq 10$, for example, 1, 2, 3, 4, or 5. In particular, q is $1 \leq q \leq 10$, for example, 1, 2, 3, 4 or 5. More in particular q is 2.

According to particular examples, the compound of formula $(M_1)_j(M_2)_kX_n:(M_3)_q$ may be selected from the group consisting of: $NaM_2F_4:(M_3)_q$, $LiM_2F_4:(M_3)_q$, $KM_2F_4:(M_3)_q$, $RbM_2F_4:(M_3)_q$, $CsM_2F_4:(M_3)_q$, $BeM_2F_5:(M_3)_q$, $Be(M_2)_2F_8:(M_3)_q$, $MgM_2F_5:(M_3)_q$, $Mg(M_2)_2F_8:(M_3)_q$, $CaM_2F_5:(M_3)_q$, $Ca(M_2)_2F_8:(M_3)_q$, $SrM_2F_5:(M_3)_q$, $Sr(M_2)_2F_8:(M_3)_q$, $BaM_2F_5:(M_3)_q$, $Ba(M_2)_2F_8:(M_3)_q$, $M_2F_3:(M_3)_q$, $(M_2)_2O_2S:(M_3)_q$, $(M_2)_2O_3S:(M_3)_q$, $(M_2)_2O_3:(M_3)_q$ and a combination thereof, wherein $M_2$ and $M_3$ are as defined through the whole content of the present application.

More in particular, when q is 2, the upconversion fluorescent nano-structured material according to the invention may be selected from the group consisting of: $PEI/NaYF_4$; $PEI/NaYF_4$:Yb, Er; $PEI/NaYF_4$:Yb,Tm; $PEI/NaYF_4$:Yb,Ho; $PVP/NaYF_4$; $PVP/NaYF_4$:Yb,Er; $PVP/NaYF_4$:Yb,Tm; $PVP/NaYF_4$:Yb,Ho and a combination thereof.

Examples of suitable known upconversion compounds are given in Table 1.

TABLE 1

Reported lanthanide-doped up-conversion nanoparticles.

| Host Material | Absorber ion | Emitter ion | Emission(s) | Wavelength(nm) |
|---|---|---|---|---|
| Fluorides | | | | |
| $YF_3$ | Yb | Er | Blue | 411 |
| $GdF_3$ | Yb | Er | Green | 520-550 |
| $GdF_3$ | Yb | Er | Red | 665 |
| $LaF_3$ | Yb | Er | Green | 545 |
| $LaF_3$ | Yb | Tm | Blue | 475.2 |
| $LaF_3$ | Yb | Ho | Red | 657.8 |
| $NaYF_4$ | Yb | Er | green | 518-545 |
| $NaYF_4$ | Yb | Er | Red | 652-655 |
| Oxysulfides | | | | |
| $Y_2O_2S$ | Yb | Er | Green | 520-580 |
| $Y_2O_2S$ | Yb | Er | Red | 650-700 |
| $Y_2O_2S$ | Yb | Ho | Green | 550 |
| $Y_2O_2S$ | Yb | Ho | Red | 640-680 |
| $Y_2O_2S$ | Yb | Tm | Blue | 460-500 |
| $Y_2O_2S$ | Yb | Tm | Red | 640-680 |
| $Gd_2O_2S$ | Yb | Er | Green | 520-580 |
| $Gd_2O_3S$ | Yb | Er | Red | 650-700 |
| Oxides | | | | |
| $Y_2O_3$ | Yb | Er | Red | 662 |
| $La_2(MoO_4)_3$ | Yb | Er | Green | 519, 541 |
| $La_2(MoO_4)_3$ | Yb | Er | Red | 653 |
| ZnO | | Er | Green | 520-550 |

These above indicated upconversion compounds may be prepared according to standard methodologies.

Fluoride

Fluoride materials have a wide range of potential optical applications because of their high transparency arising from low-energy phonons and high ionicity, which lead to less absolute fundamental absorption with respect to oxide or sulphide materials. This is especially important for the lanthanide ions emitting in the near-infrared part of the spectrum, because they are very sensitive to quenching by high-energy vibration. The most efficient infrared-to-visible up-conversion phosphors are Yb—Er or Yb—Tm co-doped fluorides such as $NaYF_4$, $LaF_3$, $YF_3$, and $GdF_3$. All the commercially available phosphors are in bulk form usually prepared by high temperature solid-state reactions. For bioprobes, the targeted molecules (such as proteins, DNA, RNA and other biomolecules in cells or tissues) are in the range from several nanometers to tens of nanometers. It should yield high fluorescent efficiency and be re-dispersible in polar solvents, for example in water (so-called "water soluble"). Several research groups have sought alternative approaches and synthesized upconversion fluorescent nanoparticles. $LaF_3$ has been described in many literature as the material has very low vibration energies and therefore the quenching of the excited state of the rare earth ions will be minimal. In case of $NaYF_4$ nanocrystal the available phonon mode are significantly lower energy hence it is suitable for lanthanide upconversion. Almost 50% of all NIR excitation can be upconverted with suitable dopant concentration. The efficiency of $NaYF4$ depends on the phase purity (hexagonal β phase is efficient than the cubic a phase), dopant concentration (2% Er, 18% Yb:0.3% Tm, 25% Yb), ratio of Na to Y in the starting material, ad/or preparation temperature. The up-conversion fluorescent efficiency of Yb—Er and Yb—Tm codoped $NaYF_4$ nanocrystals is about seven orders of magnitude higher than that of CdSe—ZnS quantum dots, the most efficient probe ever used in multiphoton microscopy thus far, 20 times and 6 times greater than that of $La_2O_3$:Yb, Er and $La_2(MoO_4)_3$:Yb,Er respectively and two times greater than $YF_3$:Yb,$Er^{3+}$ at optimum excitation condition. Many rare earth fluoride based phosphors present up-conversion abilities to convert infrared to visible light and convert multiphotons of lower energy to single photon of higher energy have been reported.

Oxides

Up-conversion emission has been observed and studied in many oxide doped bulk materials as well. The most efficient up-conversion phosphors currently known are based on the most frequently used up-conversion ions Er3+ and $Tm^{3+}$, often in combination with $Yb^{3+}$ as a sensitizer. Up-conversion emissions of $Er^{3+}$ doped nanocrystals have been studied in different crystal structure oxide hosts such as cubic $ZrO_2$, $Y_2O_3$, $Lu_2O_3$, $BaTiO_3$, tetragonal $La_2(MoO_4)_3$, $NaLa(WO_4)_2$ and $TiO_2$. Both $Y_2O_3$ and $ZrO_2$ are considered to be suitable doping hosts for the rare-earth ions. Compared to $Y_2O_3$, $ZrO_2$ nanocrystal is chemically more stable and it does not decompose even at pH value of 3. $ZrO_2$:$Er^{3+}$ nanocrystals with required up-conversion emission can be obtained. Apart from the above some more oxide nanocrystals have been reported, for example, $YbPO_4$ and $LuPO_4$.

Oxysulfide

Rare-earth oxysulfides have been known for a long time as excellent phosphor host materials and were famous with their low phonon energy as well as high chemical and physical stability. Several methods for the preparation of oxysulfides have been reported. The $Y_2O_2S$:Yb,$Er^{3+}$ nanoparticles showed green up-conversion emission under infrared excitation (λex=980 nm) via a two-photon process. The green emission $(2H_{11/2}/^4S_{3/2} \to {}^4I_{3/2})$ was enhanced with respect to the red emission $({}^4F_{9/2} \to {}^4I_{15/2})$ with increase of the crystallite size of the nanoparticles. Distinct green and blue up-conversion emission was demonstrated under the same infrared excitation by changing the activator ions in $Y_2O_2S$ nanoparticles from $Er^{3+}$ to $Ho^{3+}$ and $Tm^{3+}$ ions, respectively. The upconverting phosphor nanoparticles with different emission under the same infrared excitation may be applied to luminescent reporter material for the detection of targeted analytes in multiplexed assays. The $Tm^{3+}$ doped yttrium oxysulfide $(Y_2O_2S)$ showed upconversion afterglow emission peak located at 545 nm when it was excited by near infrared light (798 nm). Upconversion emission (red and green) were obtained from the $Gd_2O_3$:Yb,Er and $Gd_2O_2S$:Yb,Er particles prepared in the ELM system under the same infrared excitation (λex=980 nm) via a two-photon process. Up-conversion phosphor fine particles, about 50 nm in diameter, may be used as a luminescent reporter material for immunoassays or DNA assays.

With reference to the polymer according to the invention, the polymer is any polymer suitable to the purpose of the present invention. In particular, the polymer is selected as a suitable chelating agent for controlling the growth of the nanocrystals and/or a suitable surfactant to stabilize the nanocystals and provide with a desirable surface is the key to solve the above mentioned problems.

Accordingly, the polymer may be a linear polymer or a branched polymer. A linear polymer is a polymer composed of linear macromolecules, i.e. in which the molecules form long chains without branches or cross-linked structures. A branched polymer is a two-dimensional polymer in which the molecules have been formed by branching as opposed to a linear polymer. The polymer according to the invention may be amphiphilic or hydrophilic. The polymer may be a polymer having an amino group. In particular, the polymer according to the invention may be a polymer soluble and/or dispersible in polar solvents, for example in water.

The polymer may have an average molecular weight of about 5-50 kDa, for example, about 10-40 kDa, about 15-25 kDa. In particular, the polymer has an average molecular weight of about 25 kDa. The polymer may be selected from the group consisting of: polyethylenimine (PEI), poly-l-lysine (PLL), polyvinylpyrrolidone (PVP), polyvinyl alcohol (PVA), poly(ethylene glycol) (PEG), poly(4 vinylpyridine) (P4VP), oleic acid, stearic acid, chitosan and mixtures thereof. Any other polymer known in the art and suitable for the purpose of the present invention may also be used. In particular, the polymer may be PEI, oleic acid, PVP or a mixture thereof. More in particular, the polymer is PEI or oleic acid. The nano-structured material according to the invention may comprise the polymer at a concentration of about 5-50 weight %, in particular, of about 10-25 weight %.

According to one particular aspect, there is provided the use of polyvinylpyrrolidone (PVP) as chelating agent and/or stabilizer to synthesize fluoride nanocrystals with controlled size and shape, suitable solubility in water and organic solvents, and suitable surface property. According another particular aspect, there is provided the use of polyethyleneimine (PEI) as a surfactant to synthesize fluoride nanocrystals with suitable solubility in water and suitable surface property. PVP and/or PEI may also be coated with a uniform layer of silica onto the to further stabilized fluoride nanocrystals to form a core-shell structure.

Polyvinylpyrrolidone (PVP) is an amphiphilic surfactant which can render the nanocrystals dispersible in water and organic solvents (Yang et al. 2006). Furthermore, its pyrrolidone groups can coordinate with lanthanide ions (Goodgame et al. 1988; Li et al. 2001). Polyethyleneimine (PEI) is a hydrophilic polymer with primary, secondary and tertiary amino groups (in the ratio of 1:2:1) and an overall positive charge. The positively charged amino groups stabilize the nanoparticles in solution and may also be used for covalently bonding to biomolecules.

Oleic acid is a monounsaturated omega-9 fatty acid found in various animal and vegetable sources. It has the formula $C_{18}H_{34}O_2$ (or $CH_3(CH_2)_7CH=CH(CH_2)_7COOH$). The saturated form of oleic acid is stearic acid.

In this invention, ultrafine fluoride nanocrystals with strong multi-color upconversion fluorescence, which are well dispersed in water and most commonly used organic solvents, are synthesized using PVP or PEI as a chelating agent and/or stabilizer.

The upconversion fluorescent nano-structured material according to the invention may have a structure selected from the group consisting of: spherical, hexagonal, cubic, tetragonal, rhombohedral, orthorhombic, monoclinic, triclinic and a combination thereof. For example, the upconversion fluorescent nano-structured material has a hexagonal structure. According to particular examples, the upconversion fluorescent nano-structured material may be hexagonal phase $NaYF_4$, hexagonal phase $NaYF_4$:Yb,Er, hexagonal phase $NaYF_4$:Yb,Tm or hexagonal phase $NaYF_4$:Yb,Ho.

For the purposes of the present invention, a upconversion fluorescent nano-structured material is defined as being one comprising constituents which has at least one dimension in the nanoscale. The upconversion fluorescent nano-structured material prepared from the method according to any aspect of the present invention may comprise at least one dimension having size $\leq 1000$ nm. For example, $\leq 100$ nm, in particular, $\leq 50$ nm and even more in particular, less than 50 nm. More in particular, the nano-structured material may comprise at least one dimension of size $\leq 25$ nm, and even more in particular the nano-structured material may comprise at least one dimension of size $\leq 10$ nm or $\leq 5$ nm. According to a particular aspect, the nano-structured material prepared according to any method of the invention, may comprise one, two, three, four, five, six or even more dimension(s), each dimension of size $\leq 1000$ nm, $\leq 100$ nm, $\leq 50$ nm, less than 50 nm, $\leq 25$ nm, $\leq 10$ nm or $\leq 5$ nm. According to a more particular aspect, the nano-structured material prepared according to method of the invention, may comprise one, two, three, four, five, six or even more dimension(s), each dimension of size less than 50 nm, $\leq 25$ nm, $\leq 10$ nm or $\leq 5$ nm. The dimension may refer to the average diameter of the nano-structured material. In particular, the nano-structured material is at least one nanoparticle and the average diameter of the nanoparticle(s) is $\leq 100$ nm. The nano-structured material according to any preceding claim, wherein the nano-structured material is at least one nanoparticle and the average diameter of the nanoparticle(s) is $\leq 50$ nm.

There is also provided a method of preparing at least one upconversion fluorescent nano-structured material according to any aspect of the invention, comprising: mixing ions of at least one $M_3$, in particular at least two different $M_3$, and at least one $M_2$ to obtain a mixture; adding at least one polymer to the mixture; and adding ions of at least one X. The method may further comprise adding the polymer in the presence of ions of at least one M1. Particular examples of methods of preparing upconversion fluorescent nano-structured materials according to the invention are given in the experimental part of the present application.

There is also provided a method of controlling the size and/or shape of the nano-structured material(s) by adjusting the amount of polymer in the nano-structured material.

The method according to the present invention may be carried out in the presence of at least one solvent. Solvent may be defined as being a fluid phase (such as liquid, gas or plasma) that dissolves a solid, liquid or gaseous compound, resulting in a solution. The at least one solvent may be a polar solvent. Any suitable polar solvent may be used for the present invention. For example, the polar solvent may be selected from the group consisting of: water, methanol, ethanol, propyl alcohol, butanol, pentanol, hexanol, ketone, ethylene glycol, glycerol, propylene glycol, polyethylene glycol, ethyl acetate, esters and a combination thereof.

The upconversion fluorescent nano-structured material according to the invention may be in the form of: nanoparticle(s), nanofilm or monolith. In particular, the upconversion fluorescent nano-structured material according to the invention may be a NIR-to-visible upconversion fluorescent nanoparticle. The nanofilm may have a thickness between 0.1 nm to 1 mm. In particular, the nanofilm thickness may be the same or less than 500 nm, 400 nm, 300 nm, 200 nm, 100 nm, 50 nm, 25 nm, 20 nm, 15 nm, 10 nm or 5 nm. The nanofilm may be a single layer or multiple layers, and wherein each layer of the nanofilm is the same or different from the other layer. The nanofilms may be prepared by depositing particles using methods such as dip coating or spin coating.

The upconversion fluorescent nano-structured material according to the invention may further comprise at least one surfactant, lipid, polymer, inorganic material, or a mixture thereof which is disposed about the nano-structured material and modifies the surface of the nano-structured material.

The upconversion fluorescent nanoparticle(s) according to the invention may also comprise core nanoparticle(s) and/or core-shell nanoparticle(s). The shell may be the same or different material as the core. In particular, the nano-structured material according to the invention may further comprise at least one layer of silica which is disposed about the nano-structured material and which modifies the surface of the nano-structured material. According to this embodiment the layer of silica is applied on the nano-structured material to form a core-shell structure.

The upconversion fluorescent nano-structured material according to the invention may further comprise at least one photosensitizer which is disposed about the nano-structured material and modifies the surface of the nano-structured material. The photosensitizer may be any suitable photosensitizer suitable for the purpose of the invention. In particular, the photosensitizer may be Zinc phthalocyanine (ZnPC), aminolevulinic acid (ALA), methyl aminolevulinate, temoporfin, phtalocyanine, and the like. Any other photosensitizer available in the art and suitable for the purpose of the present invention may also be used.

The upconversion fluorescent nano-structured material according to the invention may further comprise at least one biomolecule. The biomolecule may be attached to the upconversion fluorescent nano-structured material. According to a further aspect, a biomolecule may be attached to the upconversion fluorescent nano-structured material prepared from the method according to any aspect of the present invention. Therefore, the method according to any aspect of the present invention may comprise a further step of attaching a biomolecule to the upconversion fluorescent nano-structured material. The biomolecule may be attached to the nano-structured material by chemical or physical conjugation. Any suitable biomolecule may be attached to the nano-structured material. For example, the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof. In particular, the biomolecule is streptavidin, an antibody, DNA or a combination thereof. Other biomolecules with free amine, hydroxyl or carboxyl groups which could be attached to surfactants as described above include anti-cancer drugs such as carboplatin, nedaplatin, JM216, methotrexate and doxorubicin, as well as proteins and glycoproteins such as herceptin.

There is also provided at least one article of manufacture comprising the upconversion fluorescent nano-structured material according to any aspect of the invention. The article of manufacture may be at least one of the following: a display device, a solar cell, an optical data storage, a bio-probe, a carrier for drug delivery, a lamp, a LED, a LCD, a wear resistance, a laser, optical amplifier, and/or a device for bio-imaging. However, further article of manufacture know or obvious to a skilled person are also encompassed by the scope of the present invention.

There is also provided a kit comprising at least one upconversion fluorescent nano-structured material or an article of manufacture according to any one aspect of the invention. The kit may, optionally, comprise at least one biomolecule.

There is also provided at least one bio-imaging and/or bio-detection apparatus comprising: at least one nano-structured material according to any aspect of the invention; at least one biomolecule; at least one source of excitation; and at least one means for delivery of the source of excitation to the system. The source of excitation may be NIR. In particular, the NIR is at 980 nm. The means for delivery of the source of excitation to the apparatus may be selected from the group consisting of: optical fibres, endoscopes, external light and external laser.

There is also provided a upconversion fluorescent nano-structured material according to the invention for use in medicine. In particular, there is provided a upconversion fluorescent nano-structured material according to the invention for use in photodynamic therapy or for use in non-invasive imaging. In particular, the photodynamic therapy is in cancer cells. There is also provided the use of at least one upconversion fluorescent nano-structured material according to any aspect of the invention in the preparation of a medicament for photodynamic therapy.

There is also provided a method for photodynamic therapy, the method comprising the step of administering to a subject the upconversion fluorescent nano-structured material according to any aspect of the invention.

Other applications also include the use as imaging probes for high sensitivity detection, for example, high signal/noise detection on biomedical microdevices, because the upconversion phosphors are excited by NIR lasers and almost all the biological samples do not have absorption in the NIR wavelength range. So these materials have an important commercial value.

Having now generally described the invention, the same will be more readily understood through reference to the following examples which are provided by way of illustration, and are not intended to be limiting of the present invention.

EXAMPLES

All the chemical reagents were purchased from Sigma-Aldrich without further purification. All reagents were used as received without further purification. The samples were studied with a JEOL 2010F transmission electron microscope. Fluorescence spectra were recorded on a Hitachi F-500 fluorescence spectrophotometer and fluorescence images were captured using an Axiostar plus fluorescence microscope, equipped with a NIR laser (980 nm).

Example 1

Preparation of PVP/NaYF$_4$:Yb(20%),Er(2%) and PVP/NaYF$_4$:Yb(20%),Tm(2%) Nanocrystals The PVP/NaYF$_4$:Yb(20%),Er(2%) nanocrystals were synthesized as follow: Y$_2$O$_3$ (88 mg, 0.78 mmol), Yb$_2$O$_3$ (39.4 mg, 0.2 mmol) and Er$_2$O$_3$ (3.9 mg, 0.02 mmol) were dissolved in 10 mL 10% HNO$_3$, and then the solution was heated to evaporate water completely. 10 mL ethylene glycol was added to dissolve the obtained LnNO$_3$ (Ln=Y 78%, Yb 20%, Er 2%). Polyvinylpyrrolidone (PVP40, 0.5560 g) and NaCl (0.0588 g, 1 mmol) were subsequently added to the solution and heated to 80° C. until a homogeneous solution was formed. NH$_4$F (0.1482 g, 4 mmol) was dissolved in another 10 mL ethylene glycol in 80° C. and then added dropwise into the LnNO$_3$-ethylene glycol solution and maintained at 80° C.

for 10 min under stirring. The solution was then heated to 160° C. for 2 hours and cooled down to room temperature. The product was centrifuged down from the solution and washed with absolute ethanol twice.

The PVP/NaYF$_4$:Yb(20%),Tm(2%) nanocrystals were synthesized using the same protocol as described above, except that Er$_2$O$_3$ was replaced by Tm$_2$O$_3$.

Typical procedure for coating silica onto the PVP/NaYF$_4$ nanocrystals was as follow: 0.05 mmol PVP/NaYF$_4$:Yb(20%),Er(2%) nanocrystals were dispersed in 20 mL ethanol and mixed with 4 mL water and 0.5 mL ammonia (30%). 0.06 mL tetraethoxysilane (TEOS) dissolved in 10 mL ethanol was then added slowly to the solution. The product was centrifuged down and washed with water twice.

Figure 1:
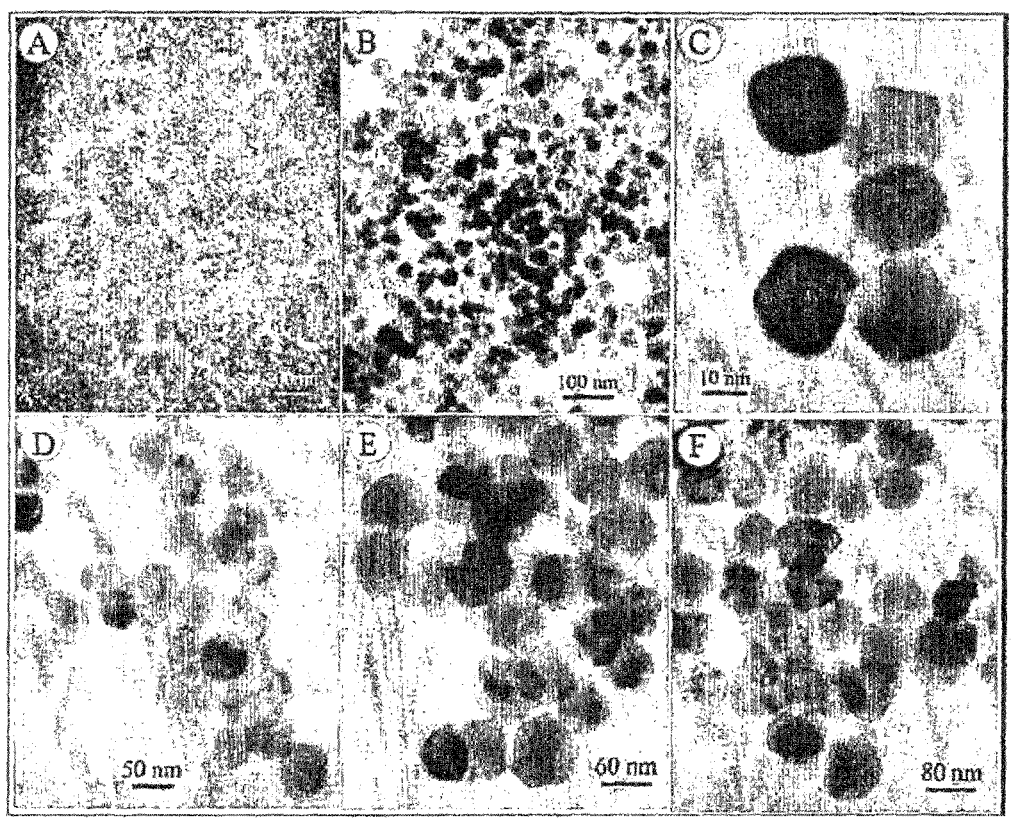
FIG. 1. TEM images of the $PVP/NaYF_4:Yb,Er$ nanocrystals with different sizes (A-C, 30 nm; D, 48 nm; E, 65 nm; F, 87 nm).
Figure 2:
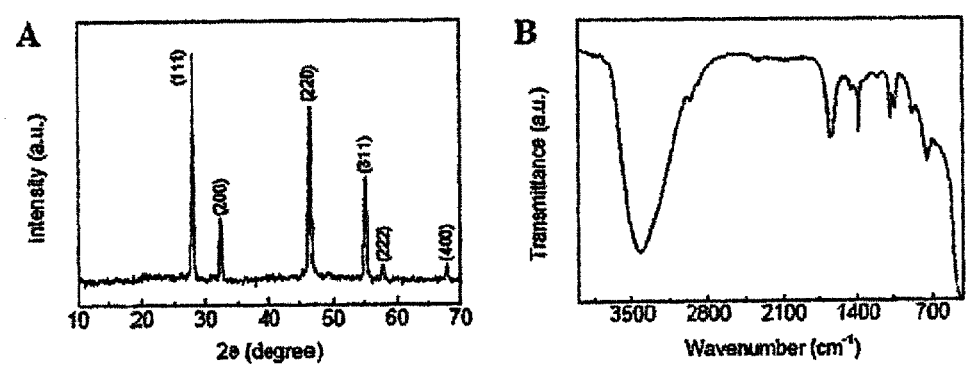
FIG. 2. XRD pattern (A) and FT-IR spectrum (B) of the $PVP/NaYF_4:Yb,Er$ nanocrystals.

FIG. 1 gives the TEM images of the PVP/NaYF$_4$:Yb,Er nanocrystals. The nanocrystals are polyhedral in shape and very uniform in size with an average size of about 30 nm (FIG. 1, A-C). The black color shown in the TEM images is due to the PVP adsorbed onto the surface of the nanocrystal which was burnt out under exposure to the accelerated electron beam during the TEM measurement. The sizes of the PVP/NaYF$_4$ nanocrystals can be altered by changing the experimental conditions such as concentrations of the reactants, reaction temperature and time. It will be obvious to a skilled person how to modify the experimental conditions so as to change the size of the nanoparticles. The sizes can be adjusted within the range of 20~140 nm with a relatively narrow size distribution. The XRD pattern of the nanocrystals given in FIG. 2 agrees well with the data for pure cubic NaYF$_4$ nanocrystals as reported in the JCPDS card (NO. 77-2042, a=5.470 Å), indicating a high purity of the NaYF$_4$ nanocrystals obtained. It was previously reported that only a mixture of cubic and hexagonal NaYF$_4$ crystals were produced in solution and heat treatment at high temperature was required to obtain pure phase NaYF$_4$ nanocrystals (Suyver et al. 2005; Yi et al. 2004). The method according to the present invention is an efficient method for producing pure phase NaYF$_4$ nanocrystals in solution at low temperature. In the FT-IR spectrum of the nanocrystals, the broad absorption band located at 3300 cm$^{-1}$ is assigned to OH$^-$ groups from the absorbed water. The characteristic IR peaks located at 1640 cm$^{-1}$ is assigned to the C=O stretching, indicating the presence of PVP on the surface of the nanocrystals (Gao et al. 2005; Liu et al. 2000). The IR peaks at 2960-2886 cm$^{-1}$ and 1388 cm$^{-1}$ corresponding to the stretching and bending of —CH$_2$ groups, and the double peaks at 1083~1042 cm$^{-1}$ corresponding to the C—N stretching, confirmed the existence of PVP on the nanocrystals. It was reported that the IR absorption peaks of PVP show a small red-shift when the C=O groups are bonded to metal ions (Gao et al. 2005; Liu et al. 2000). The IR absorption peaks assigned to the C=O groups of PVP/NaYF$_4$ nanocrystals red-shifted compared to that of pure PVP, indicated that the PVP was adsorbed onto the nanocrystals as a ligand coordinating with lanthanide ions. The IR peaks of the PVP were still observed even after the nanocrystals were washed with ethanol for many times, suggesting a strong binding between the PVP and the nanocrystal.

It has been demonstrated that only micro-sized NaYF$_4$ crystals can be formed if water is used as the solvent and no chelating agents are used (Yi et al. 2004; Zeng et al. 2005). Strong chelating agent ethylenediamine tetraacetic acid (EDTA) was used to form a complex with lanthanide ions to control the growth of the crystals and their size as well. According to the LaMer's model, the formation of such a complex could control the concentration of lanthanide ions in the solution, and thus help to control the nucleation and growth of the crystals. In this work, lanthanide ions were complexed with the pyrrolidone groups of PVP and then released slowly to the solution to react with fluoride ions in a viscous and weakly polar solvent ethylene glycol, and thus small nanocrystals were formed (Goodgame et al. 1988; Li et al. 2001). Furthermore, PVP could also serve as a stabilizer of the nanocrystals (Si et al. 2006).

Figure 3:
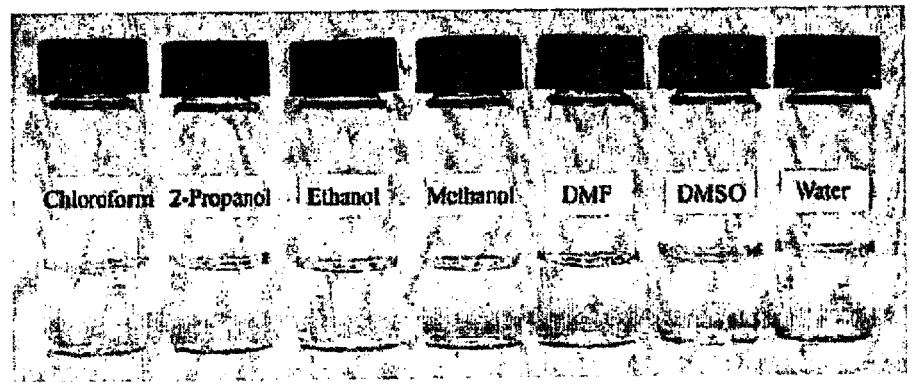
FIG. 3. Digital camera photos of the solutions of PVP-stabilized $NaYF_4:Yb$, Er NCs dispersed in different solvents. (DMF: N,N-dimethylformamide; DMSO: dimethyl sulfoxide.)

Due to the good solubility of PVP in water and many organic solvents, the PVP/NaYF$_4$ nanocrystals were well dispersed in water and many organic solvents to form colloidal solutions. Especially the nanocrystals were dispersible in water and some polar solvents such as ethanol. The photograph in FIG. 3 demonstrated that the PVP stabilized NaYF$_4$ nanocrystals are well dispersed in some most commonly used solvents, from the weakly polar solvent chloroform to strong polar solvent water, to form transparent colloidal solutions. As to non-polar solvents such as hexane, the solubility of the nanocrystals was about eight times lower than that of polar solvents. However, the nanocrystals could still be dispersed in a mixture of polar and non-polar solvents, for example, a mixture of equal amount of hexane and ethanol.

Figure 4:
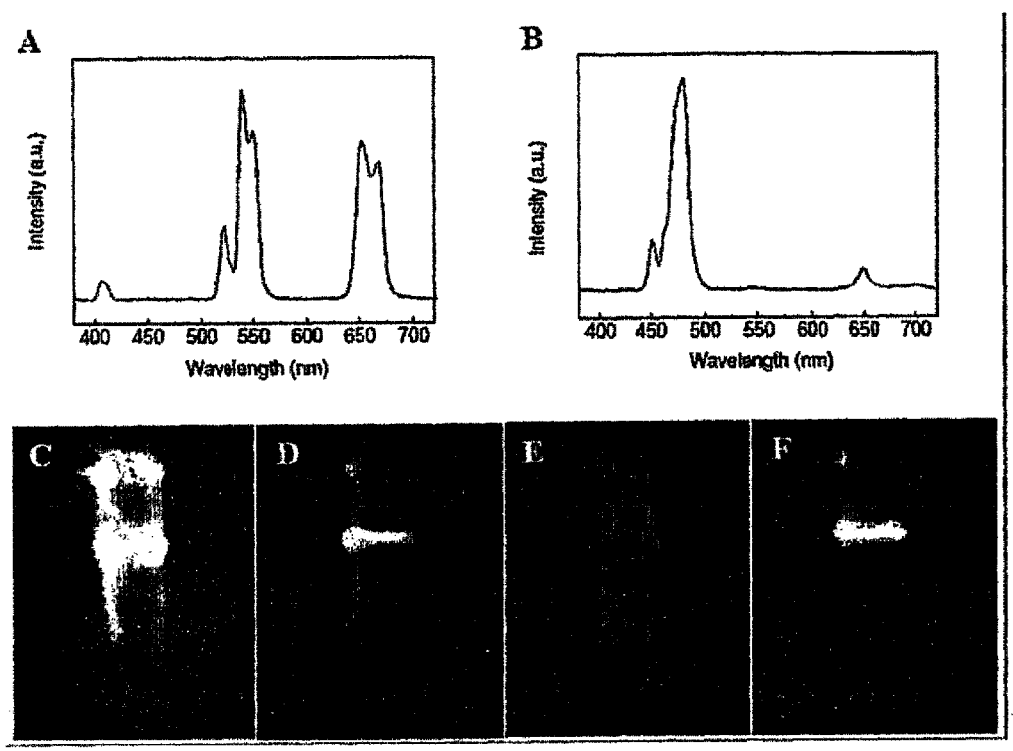
FIG. 4. Fluorescence spectra of the Yb,Er (A) and Yb,Tm (B) doped $PVP/NaYF_4$ nanocrystals in ethanol under excitation of NIR laser (980 nm), and fluorescence images of PVP/

Fluorescence spectra of the lanthanum doped PVP/NaYF$_4$ nanocrystals in ethanol solution were given in FIG. 4. The emission peaks of the PVP/NaYF$_4$:Yb,Er nanocrystals at 407 nm, 521 nm, 539 nm and 651 nm were due to the transitions from $^4H_{9/2}$, $^4H_{11/2}$, $^4S_{3/2}$, and $^4F_{9/2}$ to $^4I_{15/2}$ of Er$^{3+}$, respectively. While the emission peaks of the PVP/NaYF$_4$:Yb,Tm nanocrystals at 450 nm, 479 nm and 649 nm were assigned to the $^1D_2 \rightarrow {}^3F_4$, $^1G_4 \rightarrow {}^3H_6$ and $^1G_4 \rightarrow {}^3F_4$ transitions of Tm$^{3+}$ (Suyver et al. 2005). It is well known that the crystallinity and surface property of the nanocrystals could alter the intensity of the fluorescence emission peaks of the lanthanide ions doped. For the NaYF$_4$ nanocrystals prepared using the co-precipitation method, the intensity of the green fluorescence emission peak is much higher than the red fluorescence emission peak (Yi et al. 2004; Zeng et al. 2005), while the emission peak of red fluorescence is much more stronger than the peak of green fluorescence for the nanocrystals synthesized using oleic acid (Boyer et al. 2006). For the PVP/NaYF$_4$:Yb,Er nanocrystals, both strong green and red fluorescence were observed, indicating that either green or red fluorescence can be seen selectively using suitable filters for green or red light. Strong fluorescence with different colors from the PVP/NaYF$_4$ nanocrystals doped with Er or Tm can be seen under the excitation of 980 nm NIR laser, and the photographs are given in FIG. 4, C—F. The color of the colloidal solution of PVP/NaYF$_4$ nanocrystals could be tuned by mixing the nanocrystals doped with Er and Tm at certain ratios.

Besides the good solubility in water and organic solvents, the PVP/NaYF$_4$ nanocrystals may be coated with silica directly, while other NaYF$_4$ nanocrystals without PVP generally required some surface modifications before silica coating (Graf et al. 2006; Graf et al. 2003). The silica coating improves the photostability and biocompatibility of the nanocrystals, and the protocol for conjugation of biomolecules to silica surface has been well established (Nann and Mulvaney 2004; Yi et al. 2005; Yoon et al. 2006).

A schematic example of silica coating is given in FIG. 10. The procedure for coating silica onto the PVP/NaYF4 nanocrystals was as follows. PVP/NaYF4:Yb(20%),Er(2%) nanocrystals (0.05 mmol) were dispersed in ethanol (20 mL) and mixed with water (4 mL) and ammonia (30%, 0.5 mL). Tetraethoxysilane (TEOS, 0.06 mL) dissolved in ethanol (10 mL) was then added slowly to the solution with continuous stirring. The product was isolated by centrifugation and washed twice with water.

TEM images of the silica coated PVP/NaYF$_4$:Yb,Er nanocrystals are given in FIG. 5. Although coating of silica onto NaYF$_4$ nanocrystals was reported (Yi et al. 2004), the present inventors have demonstrated for the first time the formation of core-shell structured silica/PVP/NaYF$_4$ nanocrystals with a very uniform layer of silica on the NaYF$_4$ nanocrystals. The TEM images showed that the thickness of the silica shell was about 10 nm and could be adjusted to 1-3 nm by adding lower amount of TEOS.

The fluorescence spectra of the PVP/NaYF$_4$:Yb,Er nanocrystals before and after silica coating are given in FIG. 6. It was found that the spectra of the nanocrystals before and after silica coating looked very similar although the peak fluorescence intensity dropped a little bit after silica coating. The same was observed for the PVP/NaYF$_4$:Yb,Tm nanocrystals. The photo-stability of silica coated PVP/NaYF$_4$:Yb,Er nanocrystals was tested by measuring the fluorescence intensity of the nanocrystals in water over time and pH. The fluorescence intensity remained high over a period of 7 days without any obvious drop in the intensity, and the same was observed when the pH was changed, suggesting that the nanocrystals are quite stable in water. This makes them a very suitable fluorescent labeling material to be used for bio-applications.

Example 2

Preparation of PEI/NaYF$_4$:Yb(20%),Er (or Tm)(2%)

In another approach, PEI is used to prepare nanocrystals. In particular, PEI may be used to control the growth of NaYF$_4$ nanocrystals and to functionalize their surfaces. PEI is a highly branched polymer with an appreciable thermal stability, which makes it the polymer of choice for hydrothermal synthesis reaction.

Reagents

Polyethylenimine (PEI, (—NHCH$_2$CH$_2$—)$_x$(—N(CH$_2$CH$_2$NH$_2$)CH$_2$CH$_2$—)$_y$), sodium chloride (NaCl, >=99.0%), yttrium chloride hexahydrate (YCl$_3$.6H$_2$O, 99.99%), ytterbium oxide (Yb$_2$O$_3$, 99.99%), erbium oxide (Er$_2$O$_3$, 99.99+%), thulium oxide (Tm$_2$O$_3$, 99.99%), ammonium fluoride (NH$_4$F, 98+%), were purchased from Sigma-Aldrich. All of the reagents were used as received without further purification. PEI stock solution (5 wt %) was prepared by dissolving PEI in DI water. YCl$_3$ and NaCl stock solutions (0.2 M) were prepared by dissolving YCl$_3$.6H$_2$O and NaCl respectively in DI water. YbCl$_3$, ErCl$_3$, and TmCl$_3$ stock solutions (0.2 M) were prepared by dissolving corresponding oxides in hydrochloric acid.

Preparation of Nanocrystals

The PEI/NaYF$_4$ nanocrystals were synthesized as follow: 10 ml of NaCl, 8 ml of YCl$_3$, 1.8 ml of YbCl$_3$, and 0.2 ml of LnCl$_3$ (Ln=Er or Tm) solutions were added to 60 ml of ethanol with 20 ml of 25 kDa PEI After stirred, an appropriate amount of NH$_4$F was added. The mixture was poured into a Teflon-lined autoclave and was heated subsequently to 200° C. for 24 h with stirring. The obtained nanoparticles were collected by centrifugation, washed with ethanol and DI water for several times, and dried in vacuum. Various samples were obtained with different wt % of PEI such as 5 wt %, 10 wt %, 25 wt %, and 50 wt % PEI.

Characterization

Transmission electron microscopy (TEM) measurements were carried out on a JEOL 2010F Field Emission Electron Microscope operating at an acceleration voltage of 200 kV. A small drop of sample solution was put on a 50 Å thick carbon-coated copper grid (300 mesh) with the excess solution immediately removed. Fourier transform infrared spectroscopy (FT-IR) spectra were recorded on a Bio-Rad FTS156 spectrometer. X-ray diffraction (XRD) analysis was carried out on a ADDS wide-angle X-ray powder diffractometer with Cu—Kα radiation (40 kV, 40 mA, λ=1.54184 Å). The emission spectra were obtained with a SpectroPro 2150i spectrophotometer (Roper Scientific Acton Research, MA) equipped with a 1200 g mm-1 grating and a 980 nm diode laser.

PEI contains a large number of amino groups in the long molecular chain, which are capable of forming complexes with metal ions via coordination. High molecular weight PEI molecules can bind to the nanoparticle surface more tightly when compared to low molecular weight and thus it is more efficient to control the particle growth and stabilize the particles against aggregation. FIG. 7 shows TEM images were taken for the sample of PEI/NaYF$_4$ nanocrystals co-doped with 18% Yb$^{3+}$ and 2% Er$^{3+}$ with 5 wt %, 10 wt %, 25 wt %, 50 wt %. It was found that the particles are monodispersed and the sizes changed from 20 nm to 50 nm when the concentrations of PEI was increased from 5 wt % to 25 wt %. When the concentration was about 50 wt % PEI nanorods were seen which larger size around 400 nm.

The crystalline structure of the PEI/NaYF$_4$:Yb$^{3+}$, Er$^{3+}$ nanoparticles were determined using X-ray diffraction (XRD), and the pattern given in FIG. 8 suggested a high crystallinity of the nanoparticles. Although the hexagonal NaYF$_4$ phase (JCPDS standard card 28-1192) was a dominant phase, the XRD pattern showed that a secondary phase of cubic NaYF$_4$ (JCPDS standard card 77-2042, marked with *) was also present in the nanoparticles. The intensities of the diffraction peaks corresponding to the cubic phase increased when increasing the amount of PEI from 10 wt % to 25 wt %. The presence of the cubic phase in the nanoparticles is probably due to that PEI suppressed the formation of the hexagonal phase. It was also observed by other research groups that coordination agents could suppress the formation of hexagonal NaYF$_4$ phases (Yi et al, Nano Letters, 2004).

The mechanism of upconversion for the Yb3+, Er3+ or Yb3+, Tm3+ co-doped nanocrystals has been extensively studied (Heer et al. 2004; Suyver et al. 2005). The absorber Yb3+ ions absorb NIR light, followed by the energy transfer to the emitter Er3+ or Tm3+ ions which emit visible light. Although the emitter can be excited directly, co-doping of the absorber with ions such as Yb3+ in the nanocrystals usually generates stronger upconversion fluorescence, because Yb3+ ions have a broad and strong absorption at ~980 nm (the absorption cross-section of Yb3+ is 10 times larger than that of Er3+).

Although there were some cubic phases in the nanoparticles, which seem to be less efficient for converting NIR light to visible fluorescence than the hexagonal phases (Kramer et al. 2004), the upconversion fluorescence was fairly strong.

FIG. 9 gives the upconversion fluorescence spectra and photographs of the 25 wt % PEI/NaYF$_4$:Yb$^{3+}$,Ln$^{3+}$ (Ln: Er or Tm) nanocrystals in aqueous solutions, excited at 980 nm using a 600 mW NIR laser, showing the NIR-to-visible upconversion fluorescence from the nanocrystals. Both samples doped with Er$^{3+}$ and Tm$^{3+}$ emit bright visible fluorescence in aqueous solution.

The UC efficiency has been increased with the increase in the PEI concentration and it is represented in the graph (FIG. 10). The UC efficiency was stronger at 25 wt % PEI concentration when compared to all other samples. Further samples with 25 wt % PEI were doped with Tm. Both samples doped with Er$^{3+}$ (yellow green, red emission) and Tm$^{3+}$ (blue emission) emit bright visible fluorescence in aqueous solution. This shows that the sample with 25 wt % is very suitable to be used as fluorescent labels for bioapplications, because almost all the biological studies are carried out in aqueous solutions.

Furthermore, both samples can be efficiently excited using the same laser, emit different colors and as such they can be used for multiplexing detection.

The emission of the PEI/NaYF$_4$:Yb$^{3+}$,Er$^{3+}$ nanocrystals at 530, 550, 650, and 675 nm are a result of the transitions from $^4H_{9/2}$, $^4H_{11/2}$, $^4S_{3/2}$, and $^4F_{9/2}$ to $^4I_{15/2}$ of Er$^{3+}$, respectively. The emission peaks of the PEI/NaYF$_4$:Yb$^{3+}$,Tm$^{3+}$ nanocrystals at 450, 479, and 649 nm were assigned to the $^1D_2$ to $^3F_4$, $^1G_4$ to $^3H_6$, and $^1G_4$ to $^3F_4$ transitions of Tm$^{3+}$. It is well known that the crystallinity and surface property of the nanocrystals could alter the intensity of the fluorescence emission peaks of the doping lanthanide ions.

The fluorescence quantum yield (QY) can be defined as the ratio of photons absorbed to photons emitted. It gives the probability of deactivation of the excited state by fluorescent emission only. Usually, the QY is obtained by comparing test samples with standard samples having known QY values. The ratios of the integrated fluorescence intensities of the standard and test samples are obtained ensuring identical absorption at similar wavelengths (and hence absorbance of same number of photons), and the QY calculated. However, it is difficult to find a standard solution with known upconversion QY for purposes of comparison. Consequently, the upconversion QY of the PEI/NaYF4 nanocrystals is difficult to determine. To obtain an estimation of the upconversion efficiency, the emission intensity of the PEI/NaYF4 nanocrystals was recorded at different excitation powers (Table 2).

TABLE 2

Emission intensities under NIR excitation

| Samples | NIR laser Set at 400 mW | NIR laser Set at 200 mW |
|---|---|---|
| PEI/NaYF$_4$: Yb, Er | 60-100$^a$ mW | 20-50 mW |
| PEI/NaYF$_4$: Yb, Tm | 25-45 mW | 20-40 mW |

$^a$X-Y indicates the range of data obtained during detection.

To demonstrate the existence of PEI on the nanocrystals, Fourier transform infrared (FT-IR) measurement was performed to demonstrate the existence of PEI on the nanoparticles. FT-IR spectra of the 25 wt % PEI/NaYF$_4$:Yb$^{3+}$,Er$^{3+}$ nanocrystals (FIG. 11b) was compared with that from pure NaYF$_4$:Yb$^{3+}$,Er$^{3+}$ nanocrystals synthesized without PEI (FIG. 11a). Presence of PEI is demonstrated by the presence of the unique absorption peaks from internal vibration of amide bonds (1380-1630 cm$^{-1}$) and CH$_2$ stretching vibrations (2850-2960 cm$^{-1}$) in the spectrum of PEI/NaYF$_4$:Yb$^{3+}$, Er$^{3+}$ nanocrystals only. The presence of free amine groups on the surface of the nanocrystals is of extreme importance because they can bond to biomolecules (e.g. antibody). The intense absorption peak at about 1527 cm$^{-1}$ in FIG. 11b, corresponding to amine groups, indicated that there are still a number of free amine groups on the nanocrystals.

The development (up-conversion) UC fluorescence phosphors has been increased due its advantages such as deep tissue penetration, absence of auto fluorescence and increased chemical and photo stability. NaYF$_4$:Yb$^{3+}$, Er$^{3+}$ has higher UC efficiency when compared to others its efficiency was increased with the increase in the PEI concentration. Sample with 5 wt %, 10 wt %, 25 wt %, 50 wt % PEI were obtained. NaYF$_4$:Yb$^{3+}$,Er$^{3+}$ nanoparticles with 25 wt % PEI has been seen to be more efficient as the particle are monodispersed and around 50 nm. Samples doped with Er$^{3+}$ and Tm$^{3+}$ emit bright visible fluorescence of yellow green, red and blue respectively which shows that they can be used for multiplexing detection.

Example 3

Biocompatibility of Nanoparticles

PEI/NaYF4:Yb3+, Er3+ nanoparticles were prepared as described in example 2. Transmission electron microscope (TEM) image (FIG. 13a) showed that these are well separated particles in solution that have a mean particle size of about 50 nm with a relatively narrow size distribution. The nanoparticles were well dispersed in PBS to form a clear solution at room temperature. When excited with 980 nm NIR laser, PEI/NaYF4:Yb,Er nanoparticles emit in the visible range with two relatively sharp peaks at 500-550 nm (green light) and 650-675 nm (red light) while PEI/NaYF4:Yb,Tm nanoparticles mainly emit in the blue region. The PEI/NaYF4:Yb, Er nanoparticles were chosen for subsequent experiments.

To be used for biological studies, the nanoparticles need to be stable in PBS or physiological solutions. The nanoparticles retained maximum luminescence when stored in PBS at room temperature for several weeks (FIG. 13b). The nanoparticles were also incubated in complete fetal calf serum at 37° C. for several days. Slight reduction of fluorescence intensity was observed to about 80% of original after 12 days of incubation. This compares favorably to other nanoparticles reported in literature showing fall to 73.6% (QD705-RGD) and 66.4% (QD705) after 1 day of incubation.

For cytotoxicity test, bone marrow derived stem cells were treated with different concentrations of PEI/NaYF$_4$ nanoparticles for various periods of time, to determine the effect of both time period of incubation as well as concentration of the nanoparticles. With the nanoparticle concentration increased from 1 μg/ml to 5 μg/ml, incubation of the stem cells with the nanoparticles for 24 hours and 48 hours did not change the cell viability (FIG. 13c,d). While the nanoparticle concentration was increased to 25 μg/ml, the cell viability still remained high, above 90%. Although stem cells are very sensitive to the environment and an excellent method to demonstrate toxicity in a material, the PEI/NaYF$_4$ nanoparticles have showed no toxic effect on the cells within reasonable concentrations. Female Wistar rats were injected with the nanoparticles intravenously and the amount of Yttrium (Y) in heart, lung, spleen, kidney, liver and blood measured (FIG. 13e,f). The nanoparticles had a rapid accumulation in lungs immediately after injection, but the amount was already significantly reduced in all tissues at 24 hours post-injection with the highest concentration in the spleen. By 7 days the nanoparticles were undetectable everywhere, suggesting that the nanoparticles injected into the rats could be cleared out from the rats within one week.

Due to the presence of amino groups on the PEI/NaYF4 nanoparticles, biomolecules containing carboxyl groups could be conjugated to the nanoparticles covalently or negatively charged biomolecules could be attached to the nanoparticles through physical adsorption. Folic acid, a small molecule which can bind to over-expressed folate receptors found in a number of human solid tumors, was used as an example and conjugated to the nanoparticles through a condensation reaction between the carboxyl groups of folic acid and amino groups of PEI.

To further evaluate the biocompatibility of the nanoparticles and their applications, human colon adenocarcinoma HT-29 cells and SKBR3 cells were grown with the medium containing PEI/NaYF4:Yb3+, Er3+ nanoparticles prepared in example 2 and the cell viability was determined using the MTT assay. The nanoparticles were incubated in physiological conditions with human colonic adenocarcinoma HT29 cells and human breast cancer cell line SKBR3 for 24 hours, then unbound nanoparticles were washed away and the live cells were imaged in bright field and with NIR excitation using a confocal microscope equipped with a 980 nm NIR laser (FIG. 14).

Luminescence from the nanoparticles demonstrated a patchy distribution mainly on the surface of the cells with a high signal-to-background ratio while the control cells incubated without the nanoparticles showed no emission under similar imaging parameters. Due to the unique optical property of the upconversion nanoparticles (very low autofluorescence from biological cells under excitation of 980 nm laser), increase in the output power of the laser will increase the fluorescence signal from the nanoparticles, but not the noise.

The present inventors have demonstrated that the upconversion nanoparticles can be used for photodynamic therapy. A photosensitizer zinc pthalocyanine (ZnPC) was attached to the surface of the PEI/NaYF4:Yb,Er nanoparticles. Incident NIR laser light is upconverted by the nanoparticles to red light, which is used by the photosensitizer ZnPC to produce singlet oxygen species from dissolved molecular oxygen in the micro-environment (FIG. 15a). The nanoparticles perform three roles: it helps to solubilize the highly non-polar ZnPC, it helps to convert low energy light to higher energy radiation necessary to activate ZnPC, and finally the nanoparticles help to deliver the ZnPC to cancer cells. ZnPC was physically adsorbed to the surface of the nanoparticles by mixing ZnPC and nanoparticles in alcohol. This resulted in complete disappearance of the bluish color of the ZnPC solution. The standard curve for ZnPC fluorescence was plotted as the area of the fluorescence emission spectrum (650 nm-700 nm) versus known concentration of ZnPC in alcohol. Using the standard curve, the encapsulation efficiency of the described method was determined to be approximately 97% (FIG. 15b). High encapsulation efficiencies of ZnPC (80%) have also been demonstrated by others using PLGA nanoparticles. The fluorescence excitation spectrum of ZnPC shows an excitation maximum at about 670 nm and considerably overlaps the red emission peak for the upconversion nanoparticles (FIG. 15c). This overlap means that ZnPC in close proximity to the nanoparticles can absorb the emitted fluorescence from the nanoparticles when excited with 980 nm laser.

Production of singlet oxygen on irradiation of the ZnPC-nanoparticle complex with 980 nm was determined through the photobleaching of disodium, 9,10-anthracenedipropionic acid (ADPA, Invitrogen). Since this molecular probe is destroyed by singlet oxygen species, the concentration of ADPA—as determined by absorbance at 400 nm—is inversely proportional to the effectiveness of the energy transfer to molecular oxygen and has been used for different nanoparticle systems. The ZnPC-PEI/NaYF$_4$ nanoparticles in PBS were irradiated with a 980 nm diode laser for different time periods and absorption spectra recorded (FIG. 15d). The decreasing absorbance intensity at 400 nm demonstrated increased destruction of ADPA with time and hence the effectiveness of singlet oxygen production by the nanoparticles upon NIR excitation. Effectiveness of the nanoparticles in destruction of cancer cells was determined in vitro. Different amount of ZnPC-PEI/NaYF$_4$ nanoparticles were incubated with HT29 human colonic adenocarcinoma cells for 24 hours followed by washing away excess nanoparticles, and the cells were irradiated with 980 nm laser for 5 minutes. Cell viability, as determined using standard MTT protocol, was reduced for all concentrations incubated (FIG. 15e), indicating that the nanoparticles are useful for photodynamic therapy.

To demonstrate the ability to use the upconversion nanoparticles for non-invasive imaging and photodynamic therapy in deep tissues of animal, ARC mice and female Wistar rats were anaesthetized, fur from desired areas clipped and placed on a stage equipped with an UV lamp and NIR laser. For mice, fluorescence was seen from quantum dots (QDs) only after injected into some tissues near the body surface such as skin (FIG. 16a), however, fluorescence from the upconversion nanoparticles was seen not only from the skin (FIG. 16b), but from other tissues such as the heart (FIG. 16c), back muscles (FIG. 16d), groin muscles (FIG. 16e) and thigh muscles (FIG. 16f). For rats, fluorescence from quantum dots could not be seen from intradermal injections in thicker skin of the back (FIG. 16g), but only from the almost translucent skin of the foot (FIG. 16h). However, fluorescence from the upconversion nanoparticles was seen even after the intramuscular injection of the nanoparticles in rats (FIG. 16i,j). To compare quantum dots to upconversion nanoparticles under similar conditions, three areas on the abdomen of the rats were marked and injected respectively with 100 μl of a 4.4 mg/ml suspension of the PEI/NaYF4 nanoparticles, 100 μl of PBS and 100 μl of a commercial green emitting QD at needle penetration depths of 10 mm each. The fluorescence was recorded using CCD cameras with heat filters to eliminate NIR scatter. Fluorescence was observed from the PEI/NaYF$_4$ nanoparticle injected site upon irradiation by a 980 nm laser while no other sites showed any fluorescence (FIG. 16k,l), suggesting that the upconversion nanoparticles could be used for imaging and photodynamic therapy in deep tissues for which QDs could not be used.

Use of the upconversion nanoparticles for imaging and photodynamic therapy introduces several advantages. Optical absorption coefficients of principal tissue chromophores in the human body show a very sharp 'valley' in the NIR region and hence allow deepest tissue penetration. NIR light can penetrate depths an order of magnitude higher than visible light and can potentially be used to probe and modify deep tissue layers. NIR light is also less harmful to cells and tissues and reduces the risk of inadvertent tissue destruction. Finally, nanoparticles have a natural tendency to concentrate in tumors due to an enhanced permeation and retention effect contributed by disordered tissue architecture, increased vascularity, larger microvascular fenestrations and absence of lymphatics. This enables specific delivery of the nanoparticles to tumors which can be enhanced by other targeting molecules attached to the surface. The ability to observe the emission from the nanoparticles to some depth within tissues can have enormous impact on the diagnosis and monitoring of some tumors. NIR light, for example, can penetrate to a considerable extent in soft fibro-fatty tissues like the breast, and the upconversion nanoparticles can potentially be used for therapy as well as monitoring of tumors over time.

In conclusion, novel upconversion fluorescent nanoparticles were synthesized and used for imaging and photodynamic therapy of cancer cells. The nanoparticles convert NIR light to detectable fluorescence in the visible wavelength range and as such can be used for non-invasive imaging of cells and deep tissues in animal. They can also be used for photodynamic therapy after attaching photosensitizers to the nanoparticle surfaces. The upconversion nanoparticles could be used for non-invasive detection and photodynamic therapy of cancer or some other diseases simultaneously in deep tissues.

Methods

Synthesis and Surface Modification of PEI/NaYF$_4$ Nanoparticles

PEI/NaYF4:Yb3+, Er3+ nanoparticles were prepared as described in example 2.

To attach folic acid to the nanoparticles, 1 ml of folic acid solution (1 mM) in dimethyl sulfoxide (DMSO) was mixed with 3 ml of N-hydroxysuccinimide (NHS) (15 mM) and 3 ml of 1-ethyl-3-(3-dimethylaminopropyl)carbodiimide (EDC) (75 mM) in DI water. 1 ml of PEI/NaYF4 nanoparticles (5 mg/ml) was added. The mixture was adjusted to pH 7 and mixed overnight. The mixture was then centrifuged down and the residue was washed with PBS. Centrifugation and washing were repeated twice, and the residue was stored in PBS.

To attach zinc pthalocyanine (ZnPC) to the nanoparticles, 1 ml of ZnPC in alcohol (500 nM) was added to 1 ml of 4.4 mg/ml PEI/NaYF4 nanoparticles in alcohol and the mixture mildly shaken in an automated shaker for half an hour. The mixture was then centrifuged and the supernatant was carefully withdrawn and the particles re-suspended in PBS. The washing process was repeated twice. 2 ml of the nanoparticles suspended in PBS was put in a cuvette. Phosphorescence was measured over a range of wavelengths with a SpectroPro 2150i spectrophotometer (Roper Scientific Acton Research, MA) equipped with a 1200 g mm-1 grating and a 980 nm VA-II diode pumped solid state (DPSS) laser (current set at 1.50 A).

Cell Culture

HT29 cells (human colon adenocarcinoma cells) and SKBR3 cells (human breast cancer cells) were purchased from American Type Culture Collection (ATCC) and cultured in a media constituted of DMEM, FBS and antibiotics (streptomycin and penicillin) in a ratio of 100:10:1 in 75 cm2 flasks. Cells were incubated in a 100% humidified incubator with 5% CO2 at 37° C. Bone marrow derived stem cells were harvested from young adult female rats of the Wistar strain, 8 week old, weighing approximately 250 g. Rats were killed via cervical dislocation and the skin over the bilateral thigh area was clipped and disinfected with 70% alcohol. Under aseptic conditions, incisions were made at the lateral sides of the thighs and the skin was reflected by blunt dissection. The major muscles around the femur and tibia were dissected away. Femora and tibia were removed, cleaned of soft tissues, and placed in transport medium for 1 h. The transport medium consisted of Dulbecco's modified Eagle's medium (DMEM) plus supplemented with 10% fetal bovine serum, 500 U/ml penicillin G and 500µ/ml streptomycin. After immersing the bones in the transport medium for 1 h, containers were opened under a tissue culture hood and the femora and tibia were removed. Both ends of each femoral and tibia bones were removed with a sterile scalpel and the marrow was flushed out with 4 ml of growth medium consisting of low glucose DMEM supplemented with 10% MSC qualified fetal bovine serum, 4 mM glutamine, 50 U/ml penicillin G and 50 □g/m I streptomycin using a 25-gauge needle. Released cells were collected in a 50 ml culture tube after being suspended by repeated aspiration and expulsion from a syringe and needle. The filtrate was then centrifuged at 1,500 rpm for 8 minutes. The cell pellet, made up of different types of cells found in the bone marrow, including blood cells, contained bone marrow stem cells. The cell pellet was then re-suspended in growth medium and then plated in T-25 flasks at a 5×10$^7$ nucleated cells per flask in 5 ml of growth medium. Medium was changed after 4 days, hence removing the non-adherent cells. After 10-14 days of primary culture, the cells reached 60 to 70% confluence and were passaged using 0.5% trypsin-EDTA. The following experiments and assays described were performed with passage 4 cells. All cultures were placed in an incubator at 37° C., 95% air and 5% CO2.

MTT Assay

Cells were cultured with or without the nanoparticles and their viability was measured by MTT assay. The media was removed and cells rinsed with 300 µl of PBS twice. 50 µl of MTT solution was added to each well and topped up with 250 µl media then incubated for 1 hour. Then all media was removed. After removing the medium, the wells are washed in PBS and intracellular formazan crystals were extracted into 300 µl of DMSO and quantified by measuring the absorbance of the cell lysate at 595 nm in a microplate reader. Cell viability was expressed as a percentage of the control. All results are averages±SD of four samples.

Biodistribution in Animals

Female Wistar rats weighing about 200 to 250 g were used in compliance with the "Guide for the Care and Use of Laboratory Animals", published by the National Institute of Health, USA. Approval was also obtained from International Animal Care and Use Committee (IACUC), National University of Singapore. The rats were anaesthetized with ketamine-xylazine mixture (ketamine 75 mg/kg, xylazine 10 mg/kg) by intraperitoneal injection and then injected intravenously with the upconversion nanoparticles at a concentration of 10 µg/ml as determined by Inductively Coupled Plasma-Mass Spectrometry (ICP-MS). The rats were then euthanized at predetermined time points: 0.5 hour, 24 hours and 7 days. The heart, lung, spleen, kidney, liver and blood were collected, weighed, incubated at 37° C. overnight in digestion buffer solution containing 22.4% KOH and 2% Tween-80 while the blood sample was incubated in solution containing 89.2% potassium hydroxide (KOH) and 2% of Tween-80. Yttrium (Y) content in the samples were then determined using ICP-MS as a means of determining nanoparticle concentration.

Cell Imaging

HT29 and SKBR3 cells were cultured in a 24-well plate for 24 hours, and then PEI/NaYF4 nanoparticles (4.4 mg/ml) were added. Cells were then incubated for 1 hour at 37° C. and 4% CO2, washed thoroughly, and imaged in bright field and under infrared excitation using a Nikon confocal fluorescence microscope. The samples were excited with a specially fitted continuous wave infrared laser source (500 mW output power) and images captured using the Evolution MP Cooled Camera Kit.

Animal Imaging

ARC mice and Wistar rats were anaesthetized and fur was clipped at suitable areas. 100 µl of PEI/NaYF4 nanoparticles (4.4 mg/ml) and CdSe—ZnS quantum dots were injected subcutaneously or intramuscularly at these regions in different animals. Fluorescence was observed from excitation with a UV lamp or a 980 nm VA-II DPSS laser (current set 1.0 A) and recorded using CCD-based digital camera (Sony DSLR-A100) with heat filters to eliminate NIR scatter. The depth of injection was estimated from needle penetration. Animal-to-laser distance was fixed using a ruler attached to the laser head. At the end of the experiments, the animals were euthanized according to standard approved protocol.

Photodynamic Therapy

Production of singlet oxygen was determined through the photobleaching of disodium, 9,10-anthracenedipropionic acid (ADPA). Since this molecular probe is destroyed by singlet oxygen species, the concentration of ADPA (as determined by absorbance at 400 nm) is inversely proportional to the effectiveness of energy transfer to molecular oxygen and has been used for different nanoparticle systems. A number of wells containing equal volumes of nanoparticles (4.4 mg/ml) and ADPA (10 µM) were prepared. Each well was exposed to laser excitation at 980 nm for different time periods. Wells containing similar amount of ADPA and alcohol without the nanoparticles were used as a control. The concentration of ADPA remaining in the wells was read by measuring absorption at 400 nm using a spectrophotometer. Care was taken to keep initial concentration of ADPA the same in all wells irrespective of laser exposure. Results were expressed as percentage of the control sample without the nanoparticles. HT29 cells were plated in a 24-well plate with approximately 100,000 cells/well. Different amount of ZnPc-PEI/NaYF$_4$ nanoparticles were added to the wells (0 µl, 50 µl, 100 µl, 150 µl of 4.4 mg/ml) then topped up to 300 µl with media and the wells shaken for 0.5 hour at 37° C. The nanoparticles unattached to the cells were washed away, and the wells were then exposed to 980 nm laser for 5 minutes. Cell viability was then measured by MTT assay.

Example 4

Oleic Acid/NaYF4:Yb,Er/Tm Nanocrystals

Oleic acid was used as the surfactant to control the size and shape of the NaYF4:Yb,Er/Tm nanocrystals. The nanocrystals were prepared according to the methods described in the previous examples, with the difference that oleic acid was used instead of PEI. The nanocrystals showed different shapes when the concentration of oleic acid was changed. Transmission electron microscopy (TEM) images of the nanocrystals in FIGS. 17a and 17b showed that, when 6 mL oleic acid was added to the precursor solution, the nanocrystals were polyhedral in shape (nanospheres) with a uniform size of 21±0.5 nm in diameter. The nanospheres were easily self-assembled on the carbon grid in a long range order. The crystal lattice with an interplanar distance of 5.2 Å was shown in the high resolution TEM image in FIG. 17c, corresponding to the (100) plane of the nanocrystals. When 10 mL oleic acid was added to the precursor solution, elliptical nanocrystals with a width of 17 nm and a length of 22 nm were obtained, as shown in FIG. 17d. With the amount of oleic acid decreased to 3 mL, uniform hexagonal plate-like NaYF4:Yb,Er/Tm nanocrystals (nanoplates) were produced, as shown in FIG. 17e. The nanoplate has a flat hexagonal top surface with an edge length of ~30 nm and six rectangular side surfaces with an surface area of ~30 nm×45 nm. The crystal lattice of the nanoplate was shown in the high resolution TEM image in FIG. 1f, indicating its high crystallinity. The Fourier transform of the TEM image of single nanoplate in FIG. 1g further demonstrates a perfect hexagonal crystal structure and uniformity of the nanoplates. The X-ray diffraction (XRD) pattern and energy-dispersive X-ray analysis (EDXA) result of the hexagonal phase NaYF4:Yb,Er nanocrystals were also shown in FIG. 1. All the diffraction peaks could be indexed to pure hexagonal phase NaYF4 crystals (JCPDS standard card No. 28-1192). No diffraction peaks corresponding to cubic phase crystals or other impurities were observed. The presence of Yb and Er in the nanocrystals was confirmed by the EDXA result, and the amount of Y, Yb and Er was quantified by using inductively coupled plasma-atomic emission spectrometry (ICP-AES) and the Y/Yb/Er molar ratio determined as 79.2/18.6/2.2, close to the stoichiometric ratio for the chloride reactants used in the experiment.

Example 5

Coating of Oleic Acid/NaYF4:Yb,Er/Tm Nanocrystals with Silica

In this example, the oleic acid/NaYF4:Yb,Er/Tm nanocrystals prepared in example 4 were coated with silica.

The most commonly used methods for coating silica on nanocrystals are stober method and microemulsion method. The stober method is usually used for nanocrystals that can be well dispersed in polar solvents such as ethanol and isopropanol and as such it is not suitable for hydrophobic nanocrystals (Graf et al. 2003). Microemulsion method has been used for coating silica on hydrophobic nanocrystals such as quantum dots (QDs) and Fe$_3$O$_4$ nanoparticles, however, it is quite challenging to coat silica on individual nanoparticles, not aggregates of the nanoparticles, and make very thin silica coatings on the nanoparticles (Yi et al., 2005). To coat silica on hydrophobic oleic acid/NaYF$_4$ nanocrystals, the nanocrystals prepared in example 4 were first dispersed in cyclohexane and then surfactants and ammonia were added to form water-in-oil microemulsion. A relatively high concentration of nanocrystals was used and the emulsion was sonicated to make sure single nanocrystals were encapsulated in each microemulsion pool. It was found that such a method was very efficient for making thin and uniform silica coatings on hydrophobic oleic acid/NaYF$_4$ nanocrystals. The TEM images in FIG. 18a-c showed that this method could be used for large scale synthesis of core-shell structured NaYF$_4$ nanocrystals with a thin and uniform silica coating on the surface. The thickness of the silica shell was about 8±1.5 nm, much smaller than the diameter of the nanocrystal. After silica coating, the nanocrystals are dispersible in water with good chemical and photochemical stability and a clear colloidal solution can be formed. Furthermore, biomolecules could be conjugated to the silica surface using the well established protocols. Fluorescence spectra of transparent colloidal solutions of NaYF$_4$:Yb,Er/Tm nanospheres in hexane (0.01 M) and silica/NaYF$_4$:Yb,Er/Tm nanospheres in water (0.01 M) were given in FIGS. 18d and 18e. The emission peaks of NaYF$_4$:Yb,Er nanospheres at 407 nm, 521 nm, 539 nm and 651 nm were due to the transitions from the energy levels $^4H_{9/2}$, $^4H_{11/2}$, $^4S_{3/2}$, and $^4F_{9/2}$ to $^4I_{15/2}$ of $Er^{3+}$. Two emission peaks of NaYF$_4$:Yb,Tm nanospheres at 450 nm and 479 nm were due to $^1D_2 \rightarrow {}^3F_4$ and $^1G_4 \rightarrow {}^3H_6$ transitions of $Tm^{3+}$ (Suyver et al., 2005) The silica coated nanospheres showed a small decrease in fluorescence intensity compared to the uncoated nanospheres. The silica/NaYF4:Yb,Er nanospheres were incubated in physiological conditions with MCF-7 cells for 24 hours, and then unbound nanospheres were washed away and the live cells were imaged in bright field and with NIR excitation using a confocal microscope equipped with a 980 nm NIR laser (FIG. 19a). Fluorescence from the nanospheres was observed in the cells with a high signal-to-background ratio while the control cells incubated without the nanospheres showed no fluorescence under similar imaging parameters. Due to the unique optical property of the upconversion nanospheres (very low autofluorescence from biological cells under excitation of 980 nm laser), increase in the output power of the laser increases the fluorescence signal from the nanospheres, but not the noise (FIG. 19b).

NaYF$_4$ nanocrystals with different color upconversion fluorescence can be obtained by doping various upconverting lanthanide ions into the nanocrystals. So far only the nanocrystals co-doped with Yb/Er or Yb/Tm have been produced, which emit green or blue fluorescence with sufficiently high upconversion efficiency. The absorber Yb ions absorb NIR light, followed by the energy transfer to the emitter Er/Tm ions which emit visible light. Although the emitter can be excited directly, co-doping of the absorber such as Yb ions into the nanocrystals usually generates stronger upconversion fluorescence, because Yb ions have a broad and strong absorption at ~980 nm (the absorption cross-section of Yb is 10 times larger than that of Er/Tm). However, the nanocrystals are not suitable for multiplexing biodetection due to limited number of colors. In order to develop upconversion nanoparticles with multicolor fluorescence emission under NIR excitation at the same wavelength the present inventors prepared core-shell structured nanospheres with the upconversion nanocyrstals as the core and multicolor downconversion materials such as fluorescent dyes or quantum dots doped into the shell. The upconversion nanocrystals were used as energy donors and downconversion materials were used as energy acceptors. The upconversion nanocrystals (the core) absorb NIR radiation at single wavelength and emitted visible fluorescence is absorbed by downconversion materials (in the shell) to emit multicolor fluorescence, as shown in FIG. 20a. Two commonly used fluorescent dyes, fluorescein isothiocyanate (FITC) and tetramethylrhodamine isothiocyanate (TRITC), and quantum dot QD605 are encapsulated into the silica shell of silica/$NaYF_4$:Yb,Er/Tm nanospheres and used as examples to prove the concept. Stability of the dyes in silica is improved by grafted to an amino silane, (3-aminopropyl)triethoxysilane (APS), and then co-hydrolyzed with TEOS when making silica coatings on the upconversion nanospheres by using microemulsion method. The morphology of FITC doped silica/oleic acid/$NaYF_4$:Yb,Tm, TRITC doped silica/oleic acid/$NaYF_4$:Yb,Er, and QD605 doped silica/oleic acid/$NaYF_4$:Yb,Tm nanospheres were shown in FIG. 20b-d, similar to undoped nanospheres. The high resolution TEM image in FIG. 20d demonstrated the presence of quantum dots in silica shell. The fluorescence spectra of FITC and QD605 doped silica/$NaYF_4$:Yb,Tm nanospheres were given in FIG. 20e. The characteristic emission peaks of undoped silica/oleic acid/$NaYF_4$:Yb,Tm nanospheres at 450 nm and 479 nm were reduced, while new emission peaks of FITC and QD605 at 536 nm and 605 nm respectively appeared, indicating an efficient FRET between the nanocrystals and dyes (QD605). Similar results were observed for TRITC doped silica/oleic acid/NaYF4:Yb,Er nanospheres, as shown in FIG. 20f. The red emission peak at 651 nm was unchanged, because the fluorescence emitted at this wavelength was not absorbed by TRITC. The spectra of silica/oleic acid/$NaYF_4$:Yb,Er nanospheres doped with different amount of TRITC were given in FIG. 4g. The fluorescence intensity is proportional to the amount of TRITC doped. Strong fluorescence with different colors from silica/oleic acid/NaYF4:Yb,Er/Tm nanospheres and the nanospheres doped with FITC, TRITC and QD605 was observed under excitation of 980 nm NIR laser, and the photographs were given in FIGS. 20h and 20i. The fluorescence could still be observed even when the power density of the laser was reduced to 1 W cm-2. The strong fluorescence was probably due to the high crystallinity and uniformity of the nanocrystals. In conclusion, facile and user-friendly methods were developed to synthesize pure hexagonal-phase oleic acid/$NaYF_4$:Yb,Er/Tm nanospheres and core-shell structured nanospheres with very thin and uniform silica coatings on the surface. The nanospheres emit strong NIR-to-visible upconversion fluorescence and are used as fluorescent probes for imaging of cells. Multicolor upconversion nanospheres are produced by encapsulating organic dyes or quantum dots into the silica shell and upconversion fluorescence was generated based on fluorescence resonance energy transfer (FRET) from the $NaYF_4$ core to organic dyes or quantum dots.

Experimental Section

Synthesis of NaYF4:Yb, Er/Tm nanocrystals: All the chemicals used were purchased from Sigma-Aldrich without further purification. $NaYF_4$:18% Yb, 2% Er nanocrystals were synthesized as follows: YCl3 (0.8 mmol), YbCl3 (0.18 mmol) and ErCl3 (0.02 mmol) were mixed with 6 mL oleic acid and 15 mL octadecene (ODE) in a 50 mL flask. The solution was heated to 160° C. to form a homogeneous solution, and then cooled down to room temperature. 10 mL methanol solution containing NaOH (2.5 mmol) and $NH_4F$ (4 mmol) was slowly added into the flask and stirred for 30 minutes. Subsequently, the solution was slowly heated to remove methanol, degassed at 100° C. for 10 minutes, and then heated to 300° C. and maintained for 1 h under Argon protection. After the solution was cooled down naturally, nanocrystals were precipitated from the solution with ethanol, and washed with ethanol/water (1:1 v/v) for three times. $NaYF_4$:25% Yb, 0.3% Tm nanocrystals were synthesized using $YCl_3$, $YbCl_3$, and $ErCl_3$ with a molar ratio of 0.75:0.25:0.003.

Coating of silica on $NaYF_4$ nanospheres: 0.1 mL CO-520, 6 mL cyclohexane and 4 mL 0.01 M $NaYF_4$ nanosphere solution in cyclohexane were mixed and stirred for 10 min. Then 0.4 mL CO-520 and 0.08 mL ammonia (wt 30%) were added and the container was sealed and sonicated for 20 min until a transparent emulsion was formed. 0.04 mL TEOS was then added into the solution, and the solution was rotated for two days at a speed of 600 rpm. Silica/$NaYF_4$ nanospheres were precipitated by adding acetone, and the nanospheres were washed with ethanol/water (1:1 v/v) twice and then stored in water.

Encapsulation of dye or QD into the silica shell: FITC or TRITC was mixed with APS (molar ratio 5:1) in ethanol to form a solution of FITC-APS or TRITC-APS with a concentration of 5 mM or 10 mM respectively. [ref 5-6] Water soluble QD605 with negatively charged carboxyl groups on the surface purchased from Invitrogen was used without modification. In the process of silica coating, APS-FITC or APS-TRITC or QD605 solution was added into the emulsion and rotated for 30 min at a speed of 600 rpm. TEOS was then added into the solution and rotated for two days. The nanospheres were precipitated by adding acetone, and the nanospheres were washed with ethanol/water (1:1 v/v) twice and then stored in water.

Cell imaging: MCF-7 cells were cultured in 25 cm2 flasks in a medium made up of DMEM, Foetal Bovine Serum (FBS) and antibiotics in a ratio of 100:10:1, and incubated in a 100% humidified incubator with 5% CO2 at 37° C. according to established procedure. Cells were collected and grown on glass coverslips for 24 hours, and silica/$NaYF_4$ nanospheres were added. The cells were incubated for 24 hours at 37° C. and 4% CO2, and then imaged in bright field and under NIR excitation using a Nikon confocal microscope. NIR excitation was with a specially fitted continuous wave infrared laser source (500 mW output power) and images captured using the Evolution MP Cooled Camera Kit.

Characterization: Transmission electron microscopy (TEM) images were recorded on a JEOL 2010F transmission electron microscope. High-resolution TEM (HRTEM) and energy-dispersive X-ray analysis (EDXA) were carried out using a JEOL 3010F TEM. X-ray powder diffraction (XRD) measurement was performed on a Siemens D5005 X-ray powder diffractometer equipped with Co—Kα radiation ($\lambda$=1.78897 Å) (the diffraction patterns are different from those obtained with Cu—Kα radiation). Fluorescence spectra were recorded on a Hitachi F-500 fluorescence spectrophotometer equipped with a commercial CW IR laser (980 nm). Fluorescence images were taken using a Sony digital camera.

REFERENCES

[1] F. Wang, W. B. Tan, Y. Zhang, X. P. Fan, M. Q. Wang, *Nanotechnology* 2006, 17, R1
[2] E. Beaurepaire, V. Buissette, M. P. Sauviat, D. Giaume, K. Lahlil, A. Mercuri, D. Casanova, A. Huignard, J. L. Martin, T. Gacoin, J. P. Boilot, A. Alexandrou, *Nano Letters* 2004, 4, 2079.

[3] H. Sertchook, D. Avnir, *Chemistry of Materials* 2003, 15, 1690.
[4] F. van de Rijke, H. Zijimans, S. Li, T. Vail, A. K. Raap, R. S, Niedbala, H. J. Tanke, *Nature Biotechnology* 2001, 19, 273.
[5] G. S. Yi, H. C. Lu, S. Y. Zhao, G. Yue, W. J. Yang, D. P. Chen, L. H. Guo, *Nano Letters* 2004, 4, 2191.
[6] J. F. Suyver, A. Aebischer, D. Biner, P. Gerner, J. Grimm, S. Heer, K. W. Kramer, C. Reinhard, H. U. Gudel, *Optical Materials* 2005, 27, 1111.
[7] K. W. Kramer, D. Biner, G. Frei, H. U. Gudel, M. P. Hehlen, S. R. Luthi, *Chemistry Of Materials* 2004, 16, 1244.
[8] S. Heer, K. Kompe, H. U. Gudel, M. Haase, *Advanced Materials* 2004, 16, 2102.
[9] D. R. Larson, W. R. Zipfel, R. M. Williams, S. W. Clark, M. P. Bruchez, F. W. Wise, W. W. Webb, *Science* 2003, 300, 1434.
[10] J. H. Zeng, J. Su, Z. H. Li, R. X. Yan, Y. D. Li, *Advanced Materials* 2005, 17, 2119.
[11] H. X. Mai, Y. W. Zhang, R. Si, Z. G. Yan, L. D. Sun, L. P. You, C. H. Yan, *Journal Of The American Chemical Society* 2006, 128, 6426.
[12] J. C. Boyer, F. Vetrone, L. A. Cuccia, J. A. Capobianco, *Journal of the American Chemical Society* 2006, 128, 7444.
[13] Y. Yang, J. R. Li, J. Mu, H. L. Rong, L. Jiang, *Nanotechnology* 2006, 17, 461.
[14] D. M. L. Goodgame, D. J. Williams, R. E. P. Winpenny, *Angewandte Chemie-International Edition In English* 1988, 27, 261.
[15] Q. Li, T. Li, J. G. Wu, *Journal Of Physical Chemistry B* 2001, 105, 12293.
[16] Y. Gao, L. Song, P. Jiang, L. F. Liu, X. Q. Yan, Z. P. Zhou, D. F. Liu, J. X. Wang, H. J. Yuan, Z. X. Zhang, X. W. Zhao, X. Y. Dou, W. Y. Zhou, G. Wang, S. S. Xie, H. Y. Chen, J. Q. Li, *Journal Of Crystal Growth* 2005, 276, 606.
[17] M. H. Liu, X. P. Yan, H. F. Liu, W. Y. Yu, *Reactive & Functional Polymers* 2000, 44, 55.
[18] R. Si, Y. W. Zhang, L. P. You, C. R. Yan, *Journal Of Physical Chemistry B* 2006, 110, 5994.
[19] C. Graf, S. Dembski, A. Hofmann, E. Ruhl, *Langmuir* 2006, 22, 5604.
[20] C. Graf, D. L. J. Vossen, A. Imhof, A. van Blaaderen, *Langmuir* 2003, 19, 6693.
[21] T. Nann, P. Mulvaney, *Angewandte Chemie-International Edition* 2004, 43, 5393.
[22] D. K. Yi, S. T. Selvan, S. S. Lee, G. C. Papaefthymiou, D. Kundaliya, J. Y. Ying, *Journal Of The American Chemical Society* 2005, 127, 4990.
[23] T. J. Yoon, K. N. Yu, E. Kim, J. S. Kim, B. G. Kim, S. H. Yun, B. H. Sohn, M. H. Cho, J. K. Lee, S. B. Park, *Small* 2006, 2, 209.

The invention claimed is:

1. An upconversion fluorescent nano-structured material comprising at least one compound of formula $(M_1)_j(M_2)_kX_n:(M_3)_q$ and at least one polymer, the polymer having a concentration of 5-25 weight %, wherein
each X is the same or different and is selected from the group consisting of: halogen, O, S, Se, Te, N, P and As;
each $M_1$, if present, is the same or different and is selected from the group consisting of: Li, Na, K, Rb, Cs, Fr, Be, Mg, Ca, Sr, Ba, Ra, O and $NH_4$;
each $M_2$ is the same or different and is a metal ion;
each $M_3$, independently, is the same or different and is selected from the group consisting of Sc, Y, La, Ce, Pr, Nd, Pm, Sm, Eu, Gd, Tb, Dy, Ho, Er, Tm, Yb and Lu;
j is $0 \leq j \leq 10$; k is $1 \leq k \leq 10$; n in $1 \leq n \leq 10$; and q is $0 \leq q \leq 10$, and wherein the polymer is on the nano-structured material.

2. The upconversion fluorescent nano-structured material according to claim 1, wherein q is 2.

3. The upconversion fluorescent nano-structured material according to claim 1, wherein $M_2$ is selected from the group consisting of: transition metal ions, inner transition metal ions, and Group I to Group VI metal ions.

4. The upconversion fluorescent nano-structured material according to claim 1, wherein the polymer has an average molecular weight of about 10-40 kDa.

5. The upconversion fluorescent nano-structured material according to claim 1, wherein the polymer is selected from the group consisting of: polyethylenimine (PEI), Poly-l-lysine (PLL), polyvinylpyrrolidone (PVP), polyvinyl alcohol (PVA), poly(ethylene glycol) (PEG), poly(4 vinylpyridine) (P4VP), oleic acid, stearic acid, chitosan and mixtures thereof.

6. The upconversion fluorescent nano-structured material according to preceding claim 1, wherein each $M_3$ is different and is selected from the group consisting of: Yb, Er, Tm and Ho.

7. The upconversion fluorescent nano-structured material according to claim 1, wherein the nano-structured material is selected from the group consisting of: $PEI/NaYF_4$; $PEI/NaYF_4:Yb,Er$; $PEI/NaYF_4:Yb,Tm$; $PEI/NaYF_4:Yb,Ho$; $PVP/NaYF_4$; $PVP/NaYF_4:Yb,Er$; $PVP/NaYF_4:Yb,Tm$; $PVP/NaYF_4:Yb,Ho$ and a combination thereof.

8. The upconversion fluorescent nano-structured material according to claim 1, wherein the nano-structured material has a crystal structure selected from the group consisting of: hexagonal, cubic, tetragonal, rhombohedral, orthorhombic, monoclinic, triclinic and a combination thereof.

9. The upconversion fluorescent nano-structured material according to claim 1, wherein the nano-structured material comprises at least one dimension of size $\leq 100$ nm.

10. The upconversion fluorescent nano-structured material according to claim 1, wherein the nano-structured material is in the form of: nanoparticle(s), nanofilm or monolith.

11. The upconversion fluorescent nano-structured material according to claim 1, further comprising at least one layer of silica which is disposed about the nano-structured material and which modifies the surface of the nano-structured material.

12. The upconversion fluorescent nano-structured material according to claim 11, wherein the at least one layer of silica is doped with a fluorescent dye or quantum dot.

13. The upconversion fluorescent nano-structured material according to any preceding claim 1, further comprising at least one photosensitizer which is disposed about the nano-structured material.

14. The upconversion fluorescent nano-structured material according to claim 1, further comprising at least one biomolecule attached to the nano-structured material.

15. The upconversion fluorescent nano-structured material according to claim 1, wherein the nano-structured material is soluble in water and/or polar solvents.

16. The upconversion fluorescent nano-structured material according to claim 1, wherein the nano-structured material is a NIR-to-visible upconversion fluorescent nanoparticle.

17. An article of manufacture comprising the upconversion fluorescent nano-structured material according to claim 1.

18. The article of manufacture according to claim 17, wherein the article of manufacture is at least one of the following: a display device, a solar cell, an optical data storage, a bio-probe, a carrier for drug delivery, a lamp, a LED, a LCD, a wear resistance, a laser, optical amplifier, and/or a device for bio-imaging.

19. The article of manufacture according to claim 17, wherein the article of manufacture is a bio-imaging and/or bio-detection apparatus comprising:
- at least one upconversion fluorescent nano-structured material according to claim 1;
- at least one biomolecule;
- at least one source of excitation; and
- at least one means for delivery of the source of excitation to the apparatus.

20. The apparatus article of manufacture according to claim 19, wherein the source of excitation is NIR.

21. The apparatus article of manufacture according to claim 20, wherein the NIR is at 980 nm.

22. The article of manufacture according to claim 19, wherein the means for delivery of the source of excitation to the apparatus is selected from the group consisting of: optical fibres, LED, endoscopes, external light and external laser.

23. A method for photodynamic therapy, non-invasive bio-imaging and/or non-invasive bio-detection, the method comprising the step of administering to a subject the nano-structured material according to claim 1.

24. A method of preparing at least one upconversion fluorescent nano-structured material as defined in claim 1, comprising:
- a. mixing ions of at least one $M_3$ and at least one $M_2$ to obtain a mixture;
- b. adding at least one polymer to the mixture; and
- c. adding ions of at least one X.

25. The method according to claim 24, further comprising adding the polymer in the presence of ions of at least one M1.

26. The upconversion fluorescent nano-structured material according to claim 1, wherein the nano-structured material is biocompatible.

* * * * *